United States Patent
Dunham et al.

(10) Patent No.: US 7,183,079 B2
(45) Date of Patent: Feb. 27, 2007

(54) COMPOSITIONS AND METHODS FOR ENHANCING DISEASE RESISTANCE IN FISH

(75) Inventors: Rex A. Dunham, Auburn, AL (US); Zhanjiang Liu, Auburn, AL (US); Gregory W. Warr, Charleston, SC (US)

(73) Assignees: Auburn University, Auburn University, AL (US); MUSC Foundation for Reseach Development, Charleston, SC (US)

( * ) Notice: Subject to any disclaimer, the term of this patent is extended or adjusted under 35 U.S.C. 154(b) by 546 days.

(21) Appl. No.: 10/702,395

(22) Filed: Nov. 5, 2003

(65) Prior Publication Data

US 2004/0139488 A1 Jul. 15, 2004

Related U.S. Application Data

(60) Provisional application No. 60/424,329, filed on Nov. 6, 2002.

(51) Int. Cl.
  C12N 5/10      (2006.01)
  C12N 15/85     (2006.01)
  C12N 15/63     (2006.01)
  C12N 15/64     (2006.01)
  C12P 21/00     (2006.01)
  C12P 21/02     (2006.01)
  A61K 48/00     (2006.01)
  A01K 61/00     (2006.01)

(52) U.S. Cl. .................. 435/69.1; 435/320.1; 435/325; 435/455; 536/23.1; 536/24.1

(58) Field of Classification Search ..................... None
See application file for complete search history.

(56) References Cited

U.S. PATENT DOCUMENTS

| | | | |
|---|---|---|---|
| 5,545,808 A | 8/1996 | Hew et al. | |
| 5,719,055 A | 2/1998 | Cooper | |
| 5,998,697 A * | 12/1999 | Devlin | 800/20 |
| 5,998,698 A | 12/1999 | Cooper et al. | |
| 6,015,713 A | 1/2000 | Wright et al. | |
| 6,156,568 A | 12/2000 | Cooper et al. | |
| 6,207,817 B1 | 3/2001 | Wu et al. | |

OTHER PUBLICATIONS

Dunham, R.A., "Enhanced Bacterial Disease Resistance of Transgenic Channel Catfish *Ictalurus punctatus* Possessing Cecropin Genes," 2002, *Mar. Biotechnol.*, pp. 338-344, vol. 4.

Kelly, D., et al., "Effect of Lytic Peptides on Selected Fish Bacterial Pathogens," *Journal of Fish Diseases*, 1990, pp. 317-321, vol. 13.

Kelly, D. G., et al., "Enhanced Disease Resistance to Enteric Septicemia in Channel Catfish, *Ictalurus punctatus*, Administered Lytic Peptide," *Journal of Applied Aquaculture*, 1994, pp. 25-34, vol. 3(1/2), the Hayworth Press, Inc., Baton Rouge, LA, US.

Yaping, W., et al., "Genetic Analysis of "all-fish" Growth Hormone Gene Transferred Carp (*Cyprinus carpio L.*) and its $F_1$ Generation," *Chinese Science Bulletin*, Jul. 2001, pp. 1174-1177, vol. 46(14).

http://www.ars.usda.gov/research/projects/projects.htm?ACCN_NO=403132&fy=2001.

http://www.ars.usda.gov/research/projects/projects.htm?ACCN_NO=403132&fy=2003.

* cited by examiner

*Primary Examiner*—David Guzo
(74) *Attorney, Agent, or Firm*—Alston & Bird LLP

(57) ABSTRACT

Compositions and methods for conferring enhanced disease resistance in a fish are provided. Compositions include novel recombinant constructs that induce transgenic expression of anti-pathogenic polypeptides, including cecropin proteins or biologically active variants thereof, in a fish. Expression of the anti-pathogenic polypeptide is under the control of novel synthetic promoters, naturally occurring fish promoters, or biologically active variants thereof. Compositions of the invention also include transgenic fish cells, fish eggs, and fish, particularly catfish, having the recombinant constructs of the invention stably integrated within their genome. Methods for expressing a polypeptide of interest within a host cell are also provided, wherein expression is under control of the synthetic promoters of the invention.

6 Claims, 6 Drawing Sheets

Preprocecropin B

Nucleotide Sequence
5'-ATGAATTTCAGCAGAATCTTCTTCTTCTTCGTGTTCGCCCTCGTGCTCGCCCTCTCTACCGTGAGCGCCGCCCCAGAACCAAA
ATGGAAAGTGTTCAAAAAATCGAGAAAATGGGAAGAAATATCAGAGAAAATGGAAAGTCGTGAAAGCCGGACCAGCCATCGCTG
TGCTCGGAGAAGCCAAAGCCCCTCTAG-3' (SEQ ID NO:12)

Amino acid sequence
MNFSRIFFFVFALVLALSTVSA\AP/EP/KWKVFKKIEKMGRNIRNGIVKAGPAIAVLGEAKAL (SEQ ID NO:11)

Catfish Ig Vh leader/Procecropin B

Nucleotide Sequence
5'-ATGCTCTCTACCAGCCTGCTCCTGCCCCTGCTCTCTTATGTGCATGGCGCCCCAGAACCAAATGGAAAGTGTT
CAAAAAATCGAGAAAATGGGAAGAAATATCAGAGAAAATGGAATCGTGAAAGCCGGACCAGCCATCGCTGTGCTCGGAGAAG
CCAAAGCCCCTCTAG-3' (SEQ ID NO:21)

Amino acid sequence
MLSTSLLLLLALLSYVHG\AP/EP/KWKVFKKIEKMGRNIRNGIVKAGPAIAVLGEAKAL (SEQ ID NO:22)

Catfish Ig Vh leader/Cecropin B

Nucleotide Sequence
5'-ATGTTATCTACATCTCTACTGCTCCTGCTGGCAGCTGCTTCCTATGTGCATGGTCAGGGACTGACTCTAGAGAAATGGAA
AGTGTTCAAAAAATCGAGAAAATGGGCAGAAACATCAGAAACGGAATCGTGAAAGCCGGACCAGCCATCGCCGTGCTCG
GAGAAGCCAAAGCCCCTCTAG-3' (SEQ ID NO:23)

Amino acid sequence
MLSTSLLLLLAAASYVHG\QGLTLEKWKVFKKIEKMGRNIRNGIVKAGPAIAVLGEAKAL (SEQ ID NO:24)

FIG. 2

Catfish Ig Vh leader/Cecropin P1

Nucleotide sequence
5'-ATGCTCTCTACCAGCTCTCCTGCCCTGCTCCTCTTACGTGCATGGCAGCTGGCTCTCTAAAACCGCCAAAAA
GCTGGAAAATAGCGCCAAAAAAAGAATCTCTGAGGGCATCGCCATCGCCATCCAGGGAGGCCCAAGATAG-3'  (SEQ ID NO:27)

Amino acid sequence
MLSTSLLLLALLSYVHGSWLSKTAKKLENSAKKRISEGIAIAIQGGPR  (SEQ ID NO:28)

FIG. 3

Nucleotide
GAATTCCTGCAGAACGGGGCGGGGATCTCGAGTTCGGGGCGGGGAACTGCAGGACTGTGTTATAAACTG
GTTCCTCAGTCAGTGTTTGTTCTGCTGTGCAGTTTCTTCCTTTGACTGTTTTGATCCGGCACCATGAATTTCAGCAGAAT
CTTCTTCTTCGTGTGTTCGCCCTGTCTCGCCCTCTACCGTGAGCGCCAGCCATCCGTGCCTTCGGAAAGTGTTCAAAAAATCGAGA
AAATGGAAGAAATATCAGAAATCGAAAATGGAATCGTGAAAGCCGGACCAGCCATCGCTGTCGGAGAAGCCAAAGCCCTCTAGAGGCCCTA
TTCTATAGTGTCACCTAAATGCTAGAGCTCGCTGATCAGCCTCGACTGTCCTTTCCTAATAAAATGAGGAAATGCATCG
GTGCCTTCCTTGACCCTGGAAGGTGCCACTCCCACTGTCCTTTCCTAATAAAATGAGGAAATGCATCG
CATTGTCTGAGTAGGTGTCATTCTATTCTGGGGACTAGTTCTAGAGCGGCCGCC   (SEQ ID NO:13)

Amino Acid
MNFSRIFFFVFALVLALSTVSAAPEPKWKVFKKIEKMGRNIIRNGIVKAGPAIAVLGEAKAL   (SEQ ID NO:11)

In the nucleotide sequence:

1-73, SpI sites (artificial promoter)
74-156, minimal promoter region from goldfish VH gene 99A
157-161, Kozak consensus cite
162-347, preprocecropin B sequence
348-554, 3' untranslated region of bovine growth hormone gene SpI sites, 15-24, 35-44, 55-64
TATA box, 81-86
Start codon, 162-164
Stop codon, 345-347
Poly(A) signal, 492-498

FIG. 4

Nucleotide

GAATTCCTGCAGAGAACGGGGCGGGGATCTCGAGTTATAAATGTTTCATCACACTTATACGCGTTTATGTAAATATCTCGAGT
TGGGACGTCCAGATCTCGAGTTATGACTCAGAACTGCAGGACTGTGTTATAAACTGGTTCCTCAGTCAGTGTTTGTGTTCT
GCTGCTGTGCAGTTTCTTTCCTTTGACTGTGTTTTGGATCCGGCACCATGAATTTCAGCAGAATCTTCTTCTTCGTGTTC
GCCCTCGTGCGCCTCGTGAGCGCCGTCTAGGAATGCGTGAAAGCCGACCAGCTCGCTGTCTCGGAGAAGCCAAAGCCCTCTAGAGGCCC
AAGAAATATCAGAAATGGAATCGTGAAATGCGTGAGCTCGCTGATCAGCCTCGATCAGCCTGTCCTTCTAGTTGCCAGCCATCTGTGTTT
TATTCTATAGTGTCACCTAAATGCTAGAGCTCGCTGATCAGCCTGTCCTCCACTGTCCTTCTAATAAAATGAGGAAATTGCATCG
GCCCCTCCCCGTGCCTCTTCGACCCTGAAGGTGCCACTGTCCTTCTAATAAAATGAGGAAATTGCATCG
CATTGTCTGAGTAGGTGTCATTCTATTCTGGGGACTAGTTCTAGAGCCGCC  (SEQ ID NO:14)

Amino Acid

MNFSRIFFFVFALVLALSTVSAAPEPKWKVFKKIEKMGRNIRNGIVKAGPAIAVLGEAKAL  (SEQ ID NO:11)

In the nucleotide sequence:

15-24 Sp1
35-53 C/EBPα
64-72 Oct
82- 92 NF-κB
102-111 AP-1
120-201 Minimal promoter region from goldfish VH gene 99A
202-207 Kozak consensus sequence
208-210 Start codon
391-393 Stop codon
208-393 Preprocecropin B coding sequence
538-544 Polyadenylation signal

FIG. 5

Nucleotide
GGTACCGGGCCCCCCCTCGAGGTCGACGGTATCGATAAGCTTGATATCGAATTGGTTTGATGAAATCGCTTAGCCTTGCTCTTCAA
ACAATCCAGCTTCCTCTTCTTCACTCTGAAGTTGCAAGAAGCAAGTGTAGCAATGTGCACGCAGCAGCCGGGTGTGTGACGCTGACC
AATCAGAGCGCAGAGCTCCGAAAGTTTACCTTTTATGGCTAGAGCCGGCATCTGCCGTCATATAAAAGAGCGCCCAGCGTCTCAGCC
TCACTTTGAGCTCCTCCACACGCAGCTAGTGCGGAATATCATCTGCCTGTAACCATTCTCTAAAGTGCACAAACCCCCAAACCTAA
GGTGAGTTGATCTTTTAAGCTTTTTACATTTTCAGCTCGCATATATCGAACGTTTAAATGTTTAAATAAAGCTAGATTAA
ATGATTAGGCTCAGTTACCGGTCTCTTTTTTTCTCATTACGTGCGAACTCTGCTTAAACTCTAGTTATTCTTTATTAATATGTGTTAT
TTTATATATGTATTTATCATAACTGTACTGGCTATGTCAGGTGGTAACTGCTAAGTGTAACGTTACGTTACTCGTTGTAGGCACGACATTG
AATGGGCCGGTGTGTTGAAATAAGTCTTCAACCCCTTTTAACCTCGGTTAACAAGATTTTAACAGCTATCAGTATGAC
TGTGCGGTTTTAAAGCCGTTAGTGAGGCACGTTGCACACTTGATGAGCCGGAATGGACCGGAAGTTCTTTATGCAGGCAGTGCTGCGCAG
GGTGTGACCTACTTTAGCTAACGTTAGCCGGCTAACCAGCATTCATCTGCCGGTAACTTGAGTCTAATATTCTCTATGTGATATCGAAG
TGATCAAAGACACGTCTGTTAGCTCACTTTAACCAACTGTAGTGAAAAAATAGCGCAGTGTGCAGCCCTTCAAGTCTCTTTCATTTAGGCTT
TATTCAATCATTTATTAACTATTAACGCGTTACTAAACGTAAGGTAACGTAGTCAGTTTTTAATAACTGGTGAAAAGTACTGGTTGGG
TTTAAATGGTGACTTATATTGTGTTGAGGGGGAAACCTTTTGATAAAGCTATATAAGGCTGAGATCGTGAAGTGACTGCAGATCGTGTAGCCTGGCATGCGTTTTGGCAGACGGCCGTTGAA
CACAGGTGCTTTAGTGAAGTCCGCTCGTGAAGTCGCTGAGGATGTAGAAATTCATTTGTGTAGAATTTAGGAGTGGCCTGGCGTCAGACTGCAG
ATTCGGTTGAGTAATTGATACCAGTTGACTCTGAACCTGCTGCTGAACCCTATGTCTCTGCTGAGTGCCACACCGCGCACAAAGCGTCTCAAACCATTGCCTTTATGG
TCGAAATCCGTTCCTTTCCTTTACTGAACTCGAACCTCCTGCCAAACCTCCTGAGGCGCCATTGTCACATCTGAGGCGCCATTGTCACACTAGCGGTCAGACTGCAG
TAATAATGAGAATGCAGAGGACTTCCTTTGTCTCTGGCACATCTGAGGCGCCATTGTCACACTAGCGGTCAGACTGCAG
ACAAACAGGAAGCTGACTCCACATGTCACATGCTGACTTCCCTGACAGCTGTGACTTGACTCTGCACTTGTCACTTGTCTAAACCGGTTTCTCA
TTCATTTACAGTTCAGCAAGTTCAGCCAAGCCCGATCCGGCACCATGAATTTCAGCAGAATTCTTCTTCTTCGCCCTCGTGCCCTCGCCCCTCTC
TACCGTGAGCGCCGCCCCAGAACCAAACAAATGGAAAGTGTTCAAAAAAATGAGAAGAAATCAGAAATCAGAAATGGAATGAGCTGAAAG
CCGGACCAGCCATGCGTGTCTCGGAGAAGCCAAAGCCTTCGGAGAAGCCAAAGCCTCGTGTTGTTGCCCTATTCTATAGTGTCACCTAAATGTCTAGAGCTCGCTGAT
CAGCCTCGACTGCTGCCTCTAGTTGCCAGCCATCTGCCCTCGTGTTGCCCCTCGTGTTGCCCTTCCTTGACCCTGAAGGTGCCACCTCCCACT
GTCCTTTCCTAATAAAATGAGGAAATTGCATCGGCCGCC  (SEQ ID NO:35)

Amino Acid
MNFSRIFFFVFALVLALSTVSAAPEPKWKVFKKIEKMGRNIRNGIVKAGPAIAVLGEAKAL    (SEQ ID NO:11)

In the Nucleotide Sequence: Carp beta actin 57-1624; 1633-1638 Kozak consensus site; 1639-1824 preproceocropin B sequence; 1825-1991, 3' untranslated region of bovine growth hormone gene; Start codon, 1639-1641; Stop codon, 1822-1824; Poly(A) signal, 1969-1975.

FIG. 6

SEQUENCE LISTING

```
<160> NUMBER OF SEQ ID NOS: 35

<210> SEQ ID NO 1
<211> LENGTH: 82
<212> TYPE: DNA
<213> ORGANISM: Carassius auratus
<220> FEATURE:
<221> NAME/KEY: misc_feature
<222> LOCATION: (0)...(0)
<223> OTHER INFORMATION: Minimal goldfish promoter

<400> SEQUENCE: 1
actgtgttat aaactggttc ctcagtcagt gtttgtgttc tgctgctgtg cagtttcttt        60
tcctttgact gtttttggat cc                                                82

<210> SEQ ID NO 2
<211> LENGTH: 10
<212> TYPE: DNA
<213> ORGANISM: Piscine
<220> FEATURE:
<221> NAME/KEY: misc_feature
<222> LOCATION: (0)...(0)
<223> OTHER INFORMATION: Piscine Sp1 binding motif

<400> SEQUENCE: 2
cggggcgggg                                                              10

<210> SEQ ID NO 3
<211> LENGTH: 161
<212> TYPE: DNA
<213> ORGANISM: Artificial Sequence
<220> FEATURE:
<223> OTHER INFORMATION: Synthetic promoter

<400> SEQUENCE: 3
gaattcctgc agaacggggc ggggatctcg agttcggggc ggggataggc gtttcggggc        60
```

```
gggggaactgc aggactgtgt tataaactgg ttcctcagtc agtgtttgtg ttctgctgct    120
gtgcagtttc ttttcctttg actgttttg gatccggcac c                         161

<210> SEQ ID NO 4
<211> LENGTH: 19
<212> TYPE: DNA
<213> ORGANISM: Piscine
<220> FEATURE:
<221> NAME/KEY: misc_feature
<222> LOCATION: (0)...(0)
<223> OTHER INFORMATION: Piscine C/EBP alpha motif

<400> SEQUENCE: 4
ataatgtttc atcacactt                                                  19

<210> SEQ ID NO 5
<211> LENGTH: 8
<212> TYPE: DNA
<213> ORGANISM: Picine
<220> FEATURE:
<221> NAME/KEY: misc_feature
<222> LOCATION: (0)...(0)
<223> OTHER INFORMATION: Oct motif

<400> SEQUENCE: 5 atgtaaat                                                              8

<210> SEQ ID NO 6
<211> LENGTH: 10
<212> TYPE: DNA
<213> ORGANISM: Piscine
<220> FEATURE:
<221> NAME/KEY: misc_feature
<222> LOCATION: (0)...(0)
<223> OTHER INFORMATION: NF-KappaB motif

<400> SEQUENCE: 6
gggacgtccc                                                            10

<210> SEQ ID NO 7
<211> LENGTH: 9
<212> TYPE: DNA
<213> ORGANISM: Piscine
<220> FEATURE:
<221> NAME/KEY: misc_feature
<222> LOCATION: (0)...(0)
<223> OTHER INFORMATION: AP-1 binding motif

<400> SEQUENCE: 7 atgactcag                                                             9

<210> SEQ ID NO 8
<211> LENGTH: 207
<212> TYPE: DNA
<213> ORGANISM: Artificial Sequence
<220> FEATURE:
<223> OTHER INFORMATION: Synthetic promoter

<400> SEQUENCE: 8
gaattcctgc agaacggggc ggggatctcg agttataatg tttcatcaca cttatacgcg    60
tttatgtaaa tatctcgagt tgggacgtcc catctcgagt tatgactcag aactgcagga    120 ctgtgtttata aactggttcc tcagtcagtg tttgtgttct gctgctgtgc agtttctttt    180
cctttgactg ttttggatc cggcacc                                         207
```

<210> SEQ ID NO 9
<211> LENGTH: 222
<212> TYPE: DNA
<213> ORGANISM: Bos taurus
<220> FEATURE:
<221> NAME/KEY: misc_feature
<222> LOCATION: (0)...(0)
<223> OTHER INFORMATION: 3' untranslated region of bovine growth hormone

<400> SEQUENCE: 9

```
agggccctat tctatagtgt cacctaaatg ctagagctcg ctgatcagcc tcgactgtgc      60
cttctagttg ccagccatct gttgtttgcc cctcccccgt gccttccttg accctggaag     120
gtgccactcc cactgtcctt tcctaataaa atgaggaaat tgcatcgcat tgtctgagta     180
ggtgtcattc tattctgggg gactagttct agagcggccg cc                        222
```

<210> SEQ ID NO 10
<211> LENGTH: 189
<212> TYPE: DNA
<213> ORGANISM: Hyalophora cecropia
<220> FEATURE:
<221> NAME/KEY: misc_feature
<222> LOCATION: (0)...(0)
<223> OTHER INFORMATION: Cecropin B1 precursor

<400> SEQUENCE: 10

```
atgaatttct caaggatatt tttcttcgtg ttcgctttgg ttctggcttt gtcaacagtt      60
tcggctgcac cggagccgaa atggaaagtc ttcaagaaaa ttgaaaaaat gggtcgcaac     120
attcgaaacg gtattgtcaa ggctggacca gcgatcgcgg ttttaggcga agccaaagcg     180
ctaggataa                                                             189
```

<210> SEQ ID NO 11
<211> LENGTH: 62
<212> TYPE: PRT
<213> ORGANISM: Hyalophora cecropia

<400> SEQUENCE: 11

```
Met Asn Phe Ser Arg Ile Phe Phe Phe Val Phe Ala Leu Val Leu Ala
 1               5                  10                  15

Leu Ser Thr Val Ser Ala Ala Pro Glu Pro Lys Trp Lys Val Phe Lys
            20                  25                  30

Lys Ile Glu Lys Met Gly Arg Asn Ile Arg Asn Gly Ile Val Lys Ala
        35                  40                  45

Gly Pro Ala Ile Ala Val Leu Gly Glu Ala Lys Ala Leu Gly
    50                  55                  60
```

<210> SEQ ID NO 12
<211> LENGTH: 186
<212> TYPE: DNA
<213> ORGANISM: Hyalophora cecropia
<220> FEATURE:
<221> NAME/KEY: misc_feature
<222> LOCATION: (0)...(0)
<223> OTHER INFORMATION: Preprocecropin DNA

<400> SEQUENCE: 12

```
atgaatttca gcagaatctt cttcttcgtg ttcgccctcg tgctcgccct ctctaccgtg      60
agcgccgccc cagaaccaaa atggaaagtg ttcaaaaaaa tcgagaaaat gggaagaaat     120
atcagaaatg gaatcgtgaa agccggacca gccatcgctg tgctcggaga agccaaagcc     180
ctctag                                                                186
```

<210> SEQ ID NO 13
<211> LENGTH: 569
<212> TYPE: DNA
<213> ORGANISM: Artificial Sequence
<220> FEATURE:
<223> OTHER INFORMATION: Synthetic promoter

<400> SEQUENCE: 13

```
gaattcctgc agaacggggc ggggatctcg agttcgggc ggggataggc gtttcggggc      60
ggggaactgc aggactgtgt tataaactgg ttcctcagtc agtgtttgtg ttctgctgct     120
gtgcagtttc ttttcctttg actgttttg gatccggcac catgaatttc agcagaatct     180
tcttcttcgt gttcgccctc gtgctcgccc tctctaccgt gagcgccgcc ccagaaccaa     240
aatggaaagt gttcaaaaaa atcgagaaaa tgggaagaaa tatcagaaat ggaatcgtga     300
aagccggacc agccatcgct gtgctcggag aagccaaagc cctctagagg gcccctattct    360
atagtgtcac ctaaatgcta gagctcgctg atcagcctcg actgtgcctt ctagttgcca     420
gccatctgtt gtttgcccct ccccgtgcc ttccttgacc ctggaaggtg ccactcccac      480
tgtcctttcc taataaaatg aggaaattgc atcgcattgt ctgagtaggt gtcattctat     540
tctgggggac tagttctaga gcggccgcc                                       569
```

<210> SEQ ID NO 14
<211> LENGTH: 615
<212> TYPE: DNA
<213> ORGANISM: Artificial Sequence
<220> FEATURE:
<223> OTHER INFORMATION: Synthetic promoter

<400> SEQUENCE: 14

```
gaattcctgc agaacggggc ggggatctcg agttataatg tttcatcaca cttatacgcg      60
tttatgtaaa tatctcgagt tgggacgtcc catctcgagt tatgactcag aactgcagga     120
ctgtgttata aactggttcc tcagtcagtg tttgtgttct gctgctgtgc agtttctttt     180
cctttgactg ttttggatc cggcaccatg aatttcagca gaatcttctt cttcgtgttc      240
gccctcgtgc tcgccctctc taccgtgagc gccgcccag aaccaaaatg gaaagtgttc      300
aaaaaaatcg agaaaatggg aagaaatatc agaaatggaa tcgtgaaagc cggaccagcc     360
atcgctgtgc tcggagaagc caaagccctc tagagggccc tattctatag tgtcacctaa     420
atgctagagc tcgctgatca gcctcgactg tgccttctag ttgccagcca tctgttgttt     480
gccctcccc cgtgccttcc ttgaccctgg aaggtgccac tcccactgtc ctttcctaat      540
aaaatgagga aattgcatcg cattgtctga gtaggtgtca ttctattctg ggggactagt     600
tctagagcgg ccgcc                                                       615
```

<210> SEQ ID NO 15
<211> LENGTH: 123
<212> TYPE: DNA
<213> ORGANISM: Hyalophora cecropia
<220> FEATURE:
<221> NAME/KEY: misc_feature
<222> LOCATION: (0)...(0)
<223> OTHER INFORMATION: Procecropin B DNA

<400> SEQUENCE: 15

```
gcaccggagc cgaaatggaa agtcttcaag aaaattgaaa aaatgggtcg caacattcga      60
aacggtattg tcaaggctgg accagcgatc gcggttttag gcgaagccaa agcgctagga     120
```

-continued

```
taa                                                                    123

<210> SEQ ID NO 16
<211> LENGTH: 40
<212> TYPE: PRT
<213> ORGANISM: Hyalophora cecropia

<400> SEQUENCE: 16

Ala Pro Glu Pro Lys Trp Lys Val Phe Lys Lys Ile Glu Lys Met Gly
 1               5                  10                  15
Arg Asn Ile Arg Asn Gly Ile Val Lys Ala Gly Pro Ala Ile Ala Val
            20                  25                  30
Leu Gly Glu Ala Lys Ala Leu Gly
        35                  40

<210> SEQ ID NO 17
<211> LENGTH: 120
<212> TYPE: DNA
<213> ORGANISM: Hyalophora cecropia
<220> FEATURE:
<221> NAME/KEY: misc_feature
<222> LOCATION: (0)...(0)
<223> OTHER INFORMATION: Procecropin B DNA variant

<400> SEQUENCE: 17
gccccagaac caaaatggaa agtgttcaaa aaaatcgaga aaatgggaag aaatatcaga     60
aatggaatcg tgaaagccgg accagccatc gctgtgctcg agaagccaa agccctctag    120

<210> SEQ ID NO 18
<211> LENGTH: 111
<212> TYPE: DNA
<213> ORGANISM: Hyalophora cecropia
<220> FEATURE:
<221> NAME/KEY: misc_feature
<222> LOCATION: (0)...(0)
<223> OTHER INFORMATION: Mature cecropin DNA

<400> SEQUENCE: 18
aaatggaaag tcttcaagaa aattgaaaaa atgggtcgca acattcgaaa cggtattgtc     60
aaggctggac cagcgatcgc ggttttaggc gaagccaaag cgctaggata a             111

<210> SEQ ID NO 19
<211> LENGTH: 36
<212> TYPE: PRT
<213> ORGANISM: Hyalophora cecropia

<400> SEQUENCE: 19

Lys Trp Lys Val Phe Lys Lys Ile Glu Lys Met Gly Arg Asn Ile Arg
 1               5                  10                  15
Asn Gly Ile Val Lys Ala Gly Pro Ala Ile Ala Val Leu Gly Glu Ala
            20                  25                  30
Lys Ala Leu Gly
        35

<210> SEQ ID NO 20
<211> LENGTH: 108
<212> TYPE: DNA
<213> ORGANISM: Hyalophora cecropia
<220> FEATURE:
<221> NAME/KEY: misc_feature
<222> LOCATION: (0)...(0)
<223> OTHER INFORMATION: Mature cecropin DNA variant

<400> SEQUENCE: 20
aaatggaaag tgttcaaaaa aatcgagaaa atgggaagaa atatcagaaa tggaatcgtg     60
aaagccggac cagccatcgc tgtgctcgga gaagccaaag ccctctag                 108
```

<210> SEQ ID NO 21
<211> LENGTH: 174
<212> TYPE: DNA
<213> ORGANISM: Artificial Sequence
<220> FEATURE:
<223> OTHER INFORMATION: Catfish Ig Vh leader/procecropin B coding sequence

<400> SEQUENCE: 21

```
atgctctcta ccagcctgct cctgctcctc gccctgctct cttatgtgca tggcgcccca      60
gaaccaaaat ggaaagtgtt caaaaaaatc gagaaaatgg gaagaaatat cagaaacgga     120
atcgtgaaag ccggaccagc catcgctgtg ctcggagaag ccaaagccct ctag           174
```

<210> SEQ ID NO 22
<211> LENGTH: 58
<212> TYPE: PRT
<213> ORGANISM: Artificial Sequence
<220> FEATURE:
<223> OTHER INFORMATION: Catfish Ig Vh leader/procecropin B

<400> SEQUENCE: 22

```
Met Leu Ser Thr Ser Leu Leu Leu Leu Ala Leu Leu Ser Tyr Val
  1               5                  10                  15
His Gly Ala Pro Glu Pro Glu Lys Trp Lys Val Phe Lys Lys Ile Glu
             20                  25                  30
Lys Met Gly Arg Asn Ile Arg Asn Gly Ile Val Lys Ala Gly Pro Ala
         35                  40                  45
Ile Ala Val Leu Gly Glu Ala Lys Ala Leu
     50                  55
```

<210> SEQ ID NO 23
<211> LENGTH: 180
<212> TYPE: DNA
<213> ORGANISM: Artificial Sequence
<220> FEATURE:
<223> OTHER INFORMATION: Catfish Ig Vh leader/cecropin B coding sequence

<400> SEQUENCE: 23

```
atgttatcta catctctact gctcctgctg gcagctgctt cctatgtgca tggtcaggga      60
ctgactctag agaaatggaa agtgttcaaa aaatcgaga aaatgggcag aaacatcaga     120
aacggaatcg tgaaagccgg accagccatc gccgtgctcg agaagccaa agccctctag     180
```

<210> SEQ ID NO 24
<211> LENGTH: 59
<212> TYPE: PRT
<213> ORGANISM: Artificial Sequence
<220> FEATURE:
<223> OTHER INFORMATION: Catfish Ig Vh leader/cecropin B

<400> SEQUENCE: 24

```
Met Leu Ser Thr Ser Leu Leu Leu Leu Ala Ala Ala Ser Tyr Val
  1               5                  10                  15
His Gly Gln Gly Leu Thr Leu Glu Lys Trp Lys Val Phe Lys Lys Ile
             20                  25                  30
Glu Lys Met Gly Arg Asn Ile Arg Asn Gly Ile Val Lys Ala Gly Pro
         35                  40                  45
Ala Ile Ala Val Leu Gly Glu Ala Lys Ala Leu
     50                  55
```

<210> SEQ ID NO 25
<211> LENGTH: 96
<212> TYPE: DNA
<213> ORGANISM: Sus scrofa
<220> FEATURE:

```
<221> NAME/KEY: misc_feature
<222> LOCATION: (0)...(0)
<223> OTHER INFORMATION: Porcine cecropin P1 coding sequence

<400> SEQUENCE: 25
agctggctct ctaaaaccgc caaaaagctg gaaaatagcg ccaaaaaaag aatctctgag    60
ggcatcgcca tcgccatcca gggaggccca agatag                              96

<210> SEQ ID NO 26
<211> LENGTH: 31
<212> TYPE: PRT
<213> ORGANISM: Sus scrofa

<400> SEQUENCE: 26

Ser Trp Leu Ser Lys Thr Ala Lys Lys Leu Glu Asn Ser Ala Lys Lys
1               5                   10                  15
Arg Ile Ser Glu Gly Ile Ala Ile Ala Ile Gln Gly Gly Pro Arg
            20                  25                  30

<210> SEQ ID NO 27
<211> LENGTH: 150
<212> TYPE: DNA
<213> ORGANISM: Artificial Sequence
<220> FEATURE:
<223> OTHER INFORMATION: Catfish Ig Vh leader/cecropin P1 coding
                        sequence

<400> SEQUENCE: 27
atgctctcta ccagcctgct cctgctcctc gccctgctct cttacgtgca tggcagctgg    60
ctctctaaaa ccgccaaaaa gctggaaaat agcgccaaaa aagaatctc tgagggcatc   120 gccatcgcca tccagggagg cccaagatag                                    150

<210> SEQ ID NO 28
<211> LENGTH: 49
<212> TYPE: PRT
<213> ORGANISM: Artificial Sequence
<220> FEATURE:
<223> OTHER INFORMATION: Catfish Ig Vh leader/cecropin P1

<400> SEQUENCE: 28

Met Leu Ser Thr Ser Leu Leu Leu Leu Ala Leu Leu Ser Tyr Val
1               5                   10                  15
His Gly Ser Trp Leu Ser Lys Thr Ala Lys Lys Leu Glu Asn Ser Ala
            20                  25                  30
Lys Lys Arg Ile Ser Glu Gly Ile Ala Ile Ala Ile Gln Gly Gly Pro
        35                  40                  45
Arg

<210> SEQ ID NO 29
<211> LENGTH: 1571
<212> TYPE: DNA
<213> ORGANISM: Cyprinos carpio
<220> FEATURE:
<221> NAME/KEY: misc_feature
<222> LOCATION: (0)...(0)
<223> OTHER INFORMATION: Carp beta-actin promoter

<400> SEQUENCE: 29
tttgatgaaa atcgcttagg ccttgctctt caaacaatcc agcttctcct tctttcactc    60
tcaagttgca agaagcaagt gtagcaatgt gcacgcgaca gccgggtgtg tgacgctgga   120
ccaatcagag cgcagagctc cgaaagttta cctttatgg ctagagccgg catctgccgt   180
catataaaag agcgcgccca gcgtctcagc ctcactttga gctcctccac acgcagctag   240
tgcggaatat catctgcctg taacccattc tctaaagtcg acaaaccccc ccaaacctaa   300
```

-continued

```
ggtgagttga tctttaagct ttttacattt tcagctcgca tatatcaatt cgaacgttta      360
attagaatgt ttaaataaag ctagattaaa tgattaggct cagttaccgg tcttttttt      420 ctcatttacg tgcgaactct gcttaaactc tagttattct ttattaatat gtggttattt      480
ttatatatgt atgttatcat aactgtactg gctatgtcag gtggtaatga ctgtaacgtt      540
acgttactcg ttgtaggcac gacattgaat gggccggtgt tgaaataagt cttcaacccc      600 tttttaacctc aaaatgtgct ctggttaaca aggattttaa cagctatcag tatgactgtg      660
cggttttaaa gccgttagtg aggcacgttg cacacttgat ggatggccgg aatgggaagt      720
tctttatgca ggcagtgctg cagcagggtg tgacctactt tagctaacgt tagccggcta      780
accagcattc atctgccggt aacttgagtc taatattctc tatgtgatat cgaagtgatc      840
aaagacacgt ctgttagctc actttaacca actgtagtga aaaatagcgc agtgtgcagc      900
ccttcaagtc tttcatttag gctgattatt caatcatttt attaactatt aacgcgttac      960
taaacgtaag gtaacgtagt cagttttaa taactggtga aaagtactgg ttgggtttaa      1020
atggtgactt ataattgtgt tggaggggga aacctttttg ataaaggcta tataatctca      1080
aatgaatggg ctgaggatgg tgttcacagg tgctttagtg aagtccgctc gtgaagagtc      1140
gctgaagtga ctgcagatct gtagcgcatg cgttttggca gacggccgtt gaaattcggt      1200
tgagtaattg ataccaggtg aggctagagg atgtagaaat tcatttgtgt agaatttagg      1260
gagtggcctg gcgtgatgaa tgtcgaaatc cgttcctttt tactgaaccc tatgtctctg      1320
ctgagtgcca caccgccggc acaaagcgtc tcaaaccatt gccttttatg gtaataatga      1380
gaatgcagag ggacttcctt tgtctggcac atctgaggcg cgcattgtca cactagcacc      1440
cactagcggt cagactgcag acaaacagga agctgactcc acatggtcac atgctcactg      1500
aagtgttgac ttccctgaca gctgtgcact ttctaaaccg gttttctcat tcatttacag      1560
ttcagccaag g                                                          1571
```

<210> SEQ ID NO 30
<211> LENGTH: 1586
<212> TYPE: DNA
<213> ORGANISM: Ictalurus punctatus
<220> FEATURE:
<221> NAME/KEY: misc_feature
<222> LOCATION: (0)...(0)
<223> OTHER INFORMATION: Channel catfish myostatin promoter

<400> SEQUENCE: 30

```
cccaatattc ccagcaggtg atcagcagag agagagacac acaggagaga tagcgagaca       60
gacagagaga aattgagaga cagacaacag agagatatag agacagagac agagagagag      120
agatatagag agacagacag agagagagag atagtagtga gacagagaga gatagagaga      180
cacagagaga gacagagaga gacatagaga gagacagaca gagagagtgt ctctcatatg      240
tcaacatatg tgtagggcat atgttgggtt ttttctgtg tgtgtgtgtg aggtaatgca      300
gaatgccaac agcaggatat attgtgggtt tggattaaac atgctcttta atttctttga      360
atacatgtta actattctat gaaacactgg agcggtagtg tagtggtagt tgcagtgtag      420
gtggtagtgg tagtggagcg gtagttgtat gtagtggcag tgttattggg agtgtagtgg      480
gagtggtagt gtagtggagc tgtagtggag tgtagtggta gtggagtata gtggtagtgt      540
agttggagtg cgtagtgtaa tgtagtggta gtgtaatatg gtgtagtggt agtgtaatgt      600
agtggtagtg gagtggtaat gtagtgtagt ggtagtggag tggtagtgta atgtagtgta      660
```

```
gtggtagtgt agtggtagtt gagcggtagt gtaatgtagt gtagtggtag tgtaatgtag      720
tgtagtggag cggtagtgta gtggtagtgg agcggtagtg taatgtagtg gagtggtagt      780
ggagcggtag tgtaatgtag tggagtggta gtggagcggt agtgtagtgg tagtggagcg      840
gtagtgtaat gtagtggagt ggtagtgtag tggtagtgta gtggtagtgg agcggtagtg      900
taatgtagtg tagtggtagt ggagcgggta gtgtagtgga gtggtagtgg agtggtagtg      960
gagtggtagt gtaatgtagt gtagttgta gtggagcggt agtgtaatgt agtggagttg     1020
gtagtggtta cggtggtagt ggagcggtag tgttaatgta gtggagtggt agtgtaatgt     1080
aggtggtagt ggtagtggag tggtagtgta atgtagtgga gtggtagtgg tagtggtagt     1140
ggagcggtag gtgtaatgta gtggagtggt agtgtaatgt agtggtagtg gtagtggagt     1200
ggtagtgtaa tgtagtggag tggtagtgga gtggtagtgt aatgtagtgg agtggtagtg     1260
tagtggtagt gtaatgtagt gtagtggaga agttgtggg tctgtctctt taaggtttca     1320
gcgctggaaa gggaggaaaa aaatccggac tgaagtccac ctctgattta ttgttgctcc     1380
gagtagccaa tcatagattt cgacgccaga gcctaaataa gagcggcgga ataatttggc     1440
ggtataaaaa ggcttttggg cgaattgaag catgacatct cgcgctacct gtccggtgtg     1500
catggcgcac ggtgttcctg ttactgctgc cacacagaaa acacaaccgc gcgcgcactc     1560
ctctctgaga cctgacctgg ctgatc                                          1586

<210> SEQ ID NO 31
<211> LENGTH: 1208
<212> TYPE: DNA
<213> ORGANISM: Ictalurus punctatus
<220> FEATURE:
<221> NAME/KEY: misc_feature
<222> LOCATION: (0)...(0)
<223> OTHER INFORMATION: Channel catfish alpha-actin promoter

<400> SEQUENCE: 31
ttctttaata aagactcgaa catctataaa atatgtattt acgtatcaat aattaataca       60
taatttaaat accaaaaata gaatatatct cccctccctc cgcggacgag ccaagcaaac      120
cctatgtatt cctttacatc tacatatgtc aaattttatg atgctactat gactgatacg      180
ctcgcatgat ccttgtggtg tggtgacgtg tctgctctct tcactttgct taactataag      240
ggaaaaccgc ctgcgtgtta acacggtttt cggggtgaaa cttttctaca acggtgcgtc      300
ctccggtttc cttgttgtcc agaaaagctg acaagactcg cgcagccgca gacaggagac      360
gccaaattgt cgtggaaatt agacaacgct cgcagactcg tcctctgaag gtaaaaaagg      420
ttttattaca gaaagccggt ttaatacagg agaggaatta agcagggag agaataatga      480 gagcgctctg aagtgcctcg tgctgaaccg ctactataga tatgaaacgc agagcacgac      540
atacttctgt atacccataa gaagcggttt gaggcagttc aaacagtttt aggatcttgg      600
aagatgttta gacgaacctc gaacagaaga acatgtttgt gtctgtacgc agataaacat      660
tctgtacgga tctcagtgac atgacatggc cctctcaggc gttatcctca gatgaacatg      720
aacaaacttc tctacacggt gtgcggtctc gggagttttg cagaattgtt cagtcatgtg      780
cactcgtgaa atccaccctg cagtacagac gatgctgagt gctgcccctt cacttataca      840
cacgtaaact gctcgtcgtg tccattagct tctttgcttg catcccattg tctctactaa      900
ctggcgtgat gaacacgtgt aatcgtaaat agaattacga tgagaaaaag tcaaatcgtt      960
gaaacccaac ctttcacgcg tgtgcttaac tatgaatgaa gtgacggtga tgccttactg     1020
agcaccttgt tctttccaca tttcaaaaaa cataacagga ggagaatttt ttttttttat     1080
```

```
ggactaaaat atatgcactt ttaatgtagt cccagtaggc ataggttaga atacacactt    1140
aggtgtattg tgtgtgtgtg tgtgtttcat tcctcatcgt gtgcttctat atcaggaacc    1200
cattcaac                                                              1208

<210> SEQ ID NO 32
<211> LENGTH: 1799
<212> TYPE: DNA
<213> ORGANISM: Ictalurus punctatus
<220> FEATURE:
<221> NAME/KEY: misc_feature
<222> LOCATION: (0)...(0)
<223> OTHER INFORMATION: Channel catfish creatine kinase promoter

<400> SEQUENCE: 32
tgtgtgtgtg tgtgtaagag tgagagatat atattaacag ctgttttgat ttggtacata     60
ttctagactg ccatggcagc tgccccagta tcagctgacc atctcttagc ctggcagatt    120
gatgcgaatg catccctacc ctgttttttcc atctccatct cccgctctct ttctcaccag   180
cacttagctg aagtcatcat ctccaatagc aagcaaagta acattcctc tcatatcctg    240 ttcactactt agcactactc agttgagtta aaccagacct tctctttcga tgtaatatca   300
attttaaggt aacaattaac attttgaagg taatataaaa tagtgcaaaa gtgagaaaat   360
tgaaaacggc actgttatat acactagtct atggaataat atacttctcg ctagcagcac   420
tatggtatta atatcaaaaa agcttttccaa gcatcctctg tccaagtgtg tctcttcagc   480
caggtagaca aaaacagtct tcccgagctg ccttctttct atttatttat ttatttgaag    540
aaaaaaaaaa atctttatcc tttttttggcc tctgaataaa aactaaatgt tagcaacacg   600
aacaaaccta aaaaaaaaaa aaaaagcagt atcaaggctg gctagttacc gtagctagtt   660
aacatttgtt ttaaaataac aacaacaata aaatcatgaa cagaatccat gagtgtcttc   720
atagtgatgt caactggaga tgctagttga aagttaaaa ctacagagct ccaaaccttg    780
gcagcctcgt agctagttcg agccattctc ttgtcaccaa ataatgcctc acttccagct   840
attgttccct atttttgaatc acataatgtg ctcaattaaa gttttgcatt aaaaatgatc   900
ttgagccaga gcaagatgac tcaggcctat agcatgaatg cccagacgaa tgtctcgaac   960
acatgcagtt tttaagaaaa gtagaaatcc gagttattca attttttttag aagcccttag  1020 gactcgacat tagattttttg cacaaaaaaa acacaaaaaa aacaggaata tggacatttt   1080
ttctcacatt tcagcagaat ctgcttcatc agctttcagt tttaggatct tcaaggatgg   1140
atgaccttac agatttataa ccatatgcct gtgcaatata aatcaagtga aatacaccct   1200
cctcctcctc ctcaaagtac ttgcatacac acacactgtg gttagcacac cttcacaatc   1260
ctatacatct tcagaaatat gctgtttttt ttacagaacg ctatgtttaa tgtattaata   1320
tatgattttt tttttccatc caaatgttcc acaatgtaca attcaagagt ttcatttcat   1380
tttaatatac aaaaattcca ttgagaagat aatgcagtga taggctcagt tcattctttt   1440
tcaaggtctt tgctggacgt gagcgctgct gcgttccctg gcacacatgg caaaactctc   1500
actcagcctt tttagccttc ataaccccccc acccccccgac ccccctaact ttcaatcctc   1560
caggcttata tggagaccta tatatggggg aggaggaggg gtctacgaga gagggccagg   1620
ccacagctgc caccccatct cagatgacgg aaatgtaaat gcaggacctg tttcgtaagc   1680
taaactgggt atcagagatg tgccctgtcc aatcgcagtc catcacgctc taaaatggac   1740
ctctggagta agcagtatat aaagctgaac tgaacccttc tccgctggtg accctatt    1799
```

<210> SEQ ID NO 33
<211> LENGTH: 272
<212> TYPE: DNA
<213> ORGANISM: Oncohynus nerka
<220> FEATURE:
<221> NAME/KEY: misc_feature
<222> LOCATION: (0)...(0)
<223> OTHER INFORMATION: Salmon metallothionein promoter

<400> SEQUENCE: 33

| | | | | | |
|---|---|---|---|---|---|
| taaataaata | taggtgtagc | cttaattaat | cgatgatcaa | cgtggtaatc | aggtttatgt | 60 |
| aacaggctat | ggaatttgga | acaatagga | aactcttcct | tgattatttt | cgcgcagtat | 120 |
| aatgaaataa | cccgggtgca | aaccctgatc | gtctgaacgc | gagactgttt | tgcacacggc | 180 |
| acccgtctgt | ccctgacgct | ataaaaacgg | tcttcgccaa | agagaaattt | aaagcttaca | 240 |
| actcacaagt | gaaattgagc | tgaaatactt | ca | | | 272 |

<210> SEQ ID NO 34
<211> LENGTH: 470
<212> TYPE: DNA
<213> ORGANISM: Oncorhynus nerka
<220> FEATURE:
<221> NAME/KEY: misc_feature
<222> LOCATION: (0)...(0)
<223> OTHER INFORMATION: Salmon histone H3 promoter

<400> SEQUENCE: 34

| | | | | | |
|---|---|---|---|---|---|
| gtaaaatcgc | tggtgcggct | gcaacttgac | tactcaaccc | ccaaaggctc | ttttaagagc | 60 |
| caaccacctg | gctcagccaa | aaaagcagtg | tcctctctct | ctatggctgg | ccaactattt | 120 |
| ggcgtgtttg | ttaaatacac | acacatatac | acggcacagt | atcaagtgcc | cacatgaggc | 180 |
| ctacatgaag | aataacaact | actaggctaa | aatgaagaga | agcgttattg | cccgtaaagt | 240 |
| gtaacgttgc | tcgcggccct | aacaaaagaa | ccaagcagcg | cctcggcgag | ggatgggggt | 300 |
| tgcattttgg | ggcgtcacgg | agaggtccga | gcctcccgtc | caatgggcgg | aggaggcctc | 360 |
| cgcaacgggc | caatcagggc | ggtgcggaga | tggtgaccaa | tcagcagacg | ccgctgccgg | 420 |
| ctttataaac | ttcacatagg | catttggagg | ctatactccg | actgtgaaag | | 470 |

<210> SEQ ID NO 35
<211> LENGTH: 1997
<212> TYPE: DNA
<213> ORGANISM: Artificial Sequence
<220> FEATURE:
<223> OTHER INFORMATION: Carp beta-actin promoter with
       preprocecropin B coding

<400> SEQUENCE: 35

| | | | | | |
|---|---|---|---|---|---|
| ggtaccgggc | cccccctcga | ggtcgacggt | atcgataagc | ttgatatcga | attgggtttg | 60 |
| atgaaaatcg | cttaggcctt | gctcttcaaa | caatccagct | tctccttctt | tcactctcaa | 120 |
| gttgcaagaa | gcaagtgtag | caatgtgcac | gcgacagccg | ggtgtgtgac | gctggaccaa | 180 |
| tcagagcgca | gagctccgaa | agtttacctt | ttatggctag | agccggcatc | tgccgtcata | 240 |
| taaagagcg | cgcccagcgt | ctcagcctca | ctttgagctc | ctccacacgc | agctagtgcg | 300 |
| gaatatcatc | tgcctgtaac | ccattctcta | agtcgacaa | accccccaa | acctaaggtg | 360 |
| agttgatctt | taagcttttt | acattttcag | ctcgcatata | tcaattcgaa | cgtttaatta | 420 |
| gaatgtttaa | ataagctag | attaaatgat | taggctcagt | taccggtctt | ttttttctca | 480 |
| tttacgtgcg | aactctgctt | aaactctagt | tattctttat | taatatgtgg | ttatttttat | 540 |

-continued

```
atatgtatgt tatcataact gtactggcta tgtcaggtgg taatgactgt aacgttacgt      600
tactcgttgt aggcacgaca ttgaatgggc cggtgttgaa ataagtcttc aacccctttt      660
aacctcaaaa tgtgctctgg ttaacaagga ttttaacagc tatcagtatg actgtgcggt     720
tttaaagccg ttagtgaggc acgttgcaca cttgatggat ggccggaatg ggaagttctt     780
tatgcaggca gtgctgcgca gggtgtgacc tactttagct aacgttagcc ggctaaccag     840
cattcatctg ccggtaactt gagtctaata ttctctatgt gatatcgaag tgatcaaaga     900
cacgtctgtt agctcacttt aaccaactgt agtgaaaaat agcgcagtgt gcagcccttc     960
aagtctttca tttaggcttt attcaatcat tttattaact attaacgcgt tactaaacgt    1020
aaggtaacgt agtcagtttt taataactgg tgaaaagtac tggttgggtt taaatggtga    1080
cttataattg tgttggaggg ggaaaccttt ttgataaagg ctatataatc tcaaatgaat    1140
gggctgagga tggtgttcac aggtgcttta gtgaagtccg ctcgtgaaga gtcgctgaag    1200
tgactgcaga tctgtagcgc atgcgttttg gcagacggcc gttgaaattc ggttgagtaa    1260
ttgataccag gtgaggctag aggatgtaga aattcatttg tgtagaattt agggagtggc    1320
ctggcgtgat gaatgtcgaa atccgttcct ttttactgaa ccctatgtct ctgctgagtg    1380
ccacaccgcc ggcacaaagc gtctcaaacc attgccttt atggtaataa tgagaatgca     1440
gagggacttc ctttgtctgg cacatctgag gcgcgcattg tcacactagc acccactagc    1500
ggtcagactg cagacaaaca ggaagctgac tccacatggt cacatgctca ctgaagtgtt    1560
gacttccctg acagctgtgc actttctaaa ccggttttct cattcattta cagttcagcc    1620
aaggcccgat ccggcaccat gaatttcagc agaatcttct tcttcgtgtt cgccctcgtg    1680
ctcgccctct ctaccgtgag cgccgcccca gaaccaaaat ggaaagtgtt caaaaaaatc    1740
gagaaaatgg gaagaaatat cagaaatgga atcgtgaaag ccggaccagc catcgctgtg    1800
ctcggagaag ccaaagccct ctagagggcc ctattctata gtgtcaccta aatgctagag    1860
ctcgctgatc agcctcgact gtgccttcta gttgccagcc atctgttgtt tgcccctccc    1920
ccgtgccttc cttgaccctg gaaggtgcca ctcccactgt cctttcctaa taaaatgagg    1980
aaattgcatc ggccgcc                                                    1997
```

COMPOSITIONS AND METHODS FOR ENHANCING DISEASE RESISTANCE IN FISH

CROSS-REFERENCE TO RELATED APPLICATIONS

This application claims the benefit of U.S. Provisional Application No. 60/424,329, filed Nov. 6, 2002, which is hereby incorporated herein by reference in its entirety.

FIELD OF THE INVENTION

The present invention relates to the field of piscine molecular biology, more particularly to regulation of gene expression and enhancing disease resistance in catfish.

BACKGROUND OF THE INVENTION

The U.S. catfish industry is valued in excess of $3.0 billion dollars, and catfish production accounts for over 70% of the total U.S. aquaculture production. Aquaculture raised catfish are vulnerable to infections. Losses to stock from these infections reduce productivity and increase consumer costs—greater than $100 million dollars each year.

Immune defense proteins found in the blood and tissue fluids of vertebrates are of two classes: antigen-specific inducible antibodies (or immunoglobulins), and antigen non-specific (or innate) defense molecules that include the antibacterial peptides, which are analogous in many ways to broad spectrum antibiotics (Marchalonis (1977) *Immunity in Evolution* (Harvard University Press); Hancock (1997) *Peptide Antibiotics* 349:418–42.) Teleost fish utilize both types of defense molecules to protect against infection. Teleosts produce IgM and IgD classes of antibodies in response to infection (Wilson and Warr (1992) *Ann. Rev. Fish Dis.* 2:201–2; Warr (1995) *Dev. Comp. Immunol.* 19:1–12; Wilson et al. (1997) *Proc. Natl. Acad. Sci. USA.* 94:4593–4597). In addition, teleosts produce and secrete broad spectrum antibacterial agents such as antibacterial peptides, not just enzymes such as lysozyme (Lemaitre et al. (1996) *Eur. J. Biochem.* 240(1):143–149; Oren and Shai (1996) *Eur. J. Biochem.* 237:303–3). Nevertheless, these combined defenses are insufficient to completely protect aquacultured fish from disease, and from a practical perspective to the modern commercial fisheries industry, the natural immune response of fish is simply inadequate.

The channel catfish *Ictalurus punctatus* is an economically significant species, as well as being perhaps the best-studied model for teleost immunity (Clem et al. (1991) in *Phylogenesis of Immunological Functions*, ed. Warr and Cohen (CRC Press, Boca Raton), pp. 1–13; Miller et al. (1994) *J. Immunol.* 152:2180–2189; Ghaffari and Lobb (1991) *J. Immunol.* 146:1037–1046; Graves et al. (1985) *J. Immunol.* 134:75–85, Warr et al. (1991) *Eur. J. Immunogenetics* 18:393–379; Warr (1995) *Dev. Comp. Immunol.* 19:1–12; Wilson et al. (1997) *Proc. Natl. Acad. Sci. USA* 94:4593–4597). Channel catfish are susceptible to a variety of bacterial infections that can have a devastating effect on the stock of a fish farm. For example, enteric septicemia (caused by *Edwardsiella ictaluri*) is a recurrent, expensive problem in the catfish industry. Researchers have tried vaccination strategies to protect catfish from enteric septicemia; however, no truly satisfactory *E. ictaluri* immunization protocol exists. In fact, vaccination strategies have been generally unsuccessful for many catfish diseases (including *E. ictaluri*), even though they have been successful for other fish species (e.g., cold water vibriosis in Atlantic salmon, *Salmo salar*; see, Holm and Jorgensen (1987) *J. Fish. Dis.* 10:85–90.

Catfish farmers have attempted to protect aquacultured fish from disease using three methods. First, they have attempted to vaccinate fish. For example, U.S. Pat. No. 4,287,179 describes immunizing fish against Enteric Redmouth by immersion in water containing killed *Y. ruckeri*. Second, catfish farmers have attempted to boost the innate immunity of aquacultured fish by administering compounds that activate the immune system non-specifically such as yeast cell wall preparations (Wang and Wang (1997) *Comp. Immunol. Microbiol. Infect. Dis* 20:261–270). U.S. Pat. No. 5,593,678 describes using protein phosphatase inhibitors prophylactically to protect teleost fish, including catfish, from microbial pathogens. Third, farmers can breed catfish that express transgenes for antibacterial peptides. The transgenic peptides confer non-specific immunity to the fish without exogenous treatments.

Each of these approaches presents difficulties. Embryos and hatchlings cannot be immunized effectively because their immune system has not matured enough to effectively respond to the vaccine. Also, immunization can be a time consuming, labor intensive, and expensive procedure especially when the route of immunization is not via immersion or feeding. Non-specific boosting of the immune system tends to be of short duration, even when it is effective. Transgenic approaches are labor intensive and expensive to develop; however, compared to the other strategies, transgenic fish are likely the best solution in the long term because transgenic fish do not need subsequent treatments to protect against disease.

Antibacterial peptides are well described in the literature. The number of structural families is very large, and it is likely that antibacterial peptides occur ubiquitously among species (Hancock (1997) *Peptide Antibiotics* 349:418–42; Hoffmann et al. (1996) *Curr. Opin. Immunol.* 8:8–13; Boman (1996) *Scand. J. Immunol.* 43:475–482; Bevins and Zasloff (1990) *Annu. Rev. Biochem.* 591:395–414; and Lehrer et al. (1993) *Annu. Rev. Immunol.* 11:105–128). Among the earliest discovered and best-studied antibacterial peptides are the cecropins, small cationic peptides originally characterized in the moth *Hyalophora cecropia* (Steiner et al. (1981) *Nature* 292:246–248). The cecropins are both bacteriocidal and bacteriostatic. In fact, researchers have demonstrated that cecropins can inhibit or kill other types of pathogens including virus, fungi, and protozoa.

Cecropins possess a number of key characteristics that are likely to be useful in aquaculture. The peptides exhibit a broad spectrum of activity against gram negative bacteria including most of the major bacterial pathogens of catfish (Kelly et al. (1990) *J. Fish Dis.* 13:317–321; Thune (1993) *Fish Medicine*, ed. Stoskopf (Saunders Co., Philadelphia), pp. 511–520). The peptides are nontoxic to eukaryotic cells (Jaynes et al. (1989) *Pept. Res.* 2:157–160). Cecropins are found ubiquitously, and sources include insects and mammals, such as the pig (Lee et al. (1989) *Proc. Natl. Acad. Sci. USA* 86:9159–9162). Finally, the peptides are well described in the literature, including their physicochemical properties and mode of action (Christensen et al. (1988) *Proc. Natl. Acad. Sci. USA* 85:5072–5076), which eliminates or reduces the need for experimentation.

Experimental evidence supports the utility of cecropins in aquaculture systems. Passively administered cecropin derivatives can protect against infection with *Edwardsiella ictaluri* (Kelly et al. (1993) *J. App. Aquaculture* 3:25–34), a major pathogen of cultured catfish (Thune (1993) in *Fish Medicine*, ed. Stoskopf (Saunders Co., Philadelphia), pp. 511–520).

Creating a catfish expressing an antibacterial peptide transgene such as cecropin has several potential advantages over conventional immunization strategies. First, the fish will express cecropin from early in development, long before the immune system has matured enough to respond to immunization. Second, a cecropin transgene can confer immunity against a broad range of pathogens, obviating the need for multiple pathogen-specific vaccination preparations and treatments. Cecropin-transgenic catfish thus alleviate two major commercial losses, the destruction of stock due to diseases, and the need for ongoing prophylactic therapy or immunization for healthy stock.

Transgenic fish are the subject of several U.S. patents. For example, U.S. Pat. No. 6,207,817 relates to DNA sequences of fish insulin-like growth factor II (IGF-II) promoter regions and recombinant IGF-II promoters, and the expression of IGF-II promoter regions and recombinant IGF-II promoters in eukaryotic cells and fish embryos.

U.S. Pat. No. 6,015,713 relates to a transgenic fish that expresses human insulin and to the uses of the transgenic insulin in the treatment of diabetes. Notably, although the fish carries a humanized insulin transgene, the fish insulin regulatory sequences that drive expression of the transgene were not modified.

U.S. Pat. No. 5,545,808 describes a transgenic salmonid fish expressing exogenous salmonid growth hormone. This patent claims a method of increasing the growth rate of salmonid fish comprising the steps of a) introducing into the germ line of a salmonid fish a gene encoding a salmonid growth hormone operably linked to a type 3 antifreeze protein promoter and b) culturing the salmonid fish under conditions wherein the salmonid fish expresses the growth hormone gene at levels that increase the rate of growth at least four times over non-transgenic controls.

Sockeye salmon growth hormone genes Types 1 and 2, and sockeye histone and metallothionein gene promoters have been isolated and sequenced as described in U.S. Pat. No. 5,998,697. Terminal sequences for the growth hormone gene were also disclosed. Vectors containing these promoter and terminal sequences (and intermediate sequences) were used to transform fish egg cells, then the transformed fish egg cells were grown into transgenic fish.

U.S. Pat. No. 5,719,055 describes a transposon-based vector, which enhances the integration of DNA into a host genome, particularly a eukaryotic genome. This vector has been used to transform mammalian and fish cells with a non-constitutively expressing transgene coding for cecropin B.

U.S. Pat. No. 6,156,568 discloses transformed animals, transformed animal cells capable of expressing exogenous lytic peptides, genes in eukaryotic cells controlled by exogenous promoters that are responsive to inducers of acute phase proteins, and transposon-based transformation vectors. The patent specifically claims a eukaryotic cell in vitro that contains a gene under the control of the wild-type cecropin B promoter, wherein the promoter is exogenous to the cell. The cells, as recited, are vertebrate and mammalian cells.

U.S. Pat. No. 5,998,698 claims a transgenic catfish having a gene encoding cecropin B operably linked to the native cecropin B promoter, where the cecropin B promoter functions to direct expression of the cecropin B gene; and where the expression of the cecropin B gene imparts resistance to pathogenic bacteria. The patent further claims a transgenic koi and bony fish having a gene encoding cecropin B.

U.S. Pat. No. 6,156,568 discloses a transgenic fish having a moth cecropin gene encoding cecropin B operably linked to the native moth cecropin B promoter. The transgenic fish were protected from a challenge with *E. ictaluri*.

Thus attempts have been made to solve the problem of disease infestation by breeding fish that express transgenes coding for anti-pathogenic proteins that kill pathogens. However, this solution has created a second problem. Transgenes are routinely expressed under a viral promoter, but because consumers are likely to perceive that fish carrying viral "fragments" are unhealthy or unsafe, consumers are unlikely to buy them despite the Food and Drug Administration's approval. Therefore, fish farmers are placed in an intractable dilemma of either being forced to bear the costs of high disease incidence or, in the event they choose to farm transgenic disease-resistant fish, being unable to sell the disease-resistant fish due to consumer perceptions.

Methods for producing transgenic fish with enhanced disease resistance and which meet with consumer and FDA approval are needed.

BRIEF SUMMARY OF THE INVENTION

Compositions and methods for conferring enhanced disease resistance in a fish are provided. Compositions include novel recombinant constructs that induce transgenic expression of anti-pathogenic polypeptides, including cecropin proteins or biologically active variants thereof, in a fish. Expression of cecropin proteins or biologically active variants thereof confers disease resistance against such pathogens as viruses, parasites, and bacteria, and can provide resistance to diseases caused by *Edwardsiella ictaluri*, *Flavobacterium columnare*, *Pseudomonas fluorescens*, and *Vibrio anguillarum*. Compositions of the invention also include transgenic fish cells, fish eggs, and fish, particularly catfish, having the recombinant constructs of the invention stably integrated within their genome.

In some embodiments, the novel recombinant constructs are expression cassettes comprising a novel synthetic promoter of the present invention operably linked to a nucleotide sequence that encodes a polypeptide of interest, particularly an anti-pathogenic polypeptide of interest. Examples of anti-pathogenic polypeptides of interest include, but are not limited to, mature cecropin proteins and the preprocecropin, procecropin, and prececropin forms thereof, as well as biologically active variants of these proteins. The recombinant constructs can encode an operably linked leader sequence to facilitate post-translational processing of the encoded cecropin protein or encoded variant thereof. In alternative embodiments, the recombinant constructs of the invention are expression cassettes that provide for enhanced expression of cecropin proteins or biologically active variants thereof using exclusively piscine promoters. Such piscine promoters include, but are not limited to, myostatin promoters, alpha-actin promoters, beta-actin promoters (e.g. FV-1 and FV2 promoters), creatine kinase promoters, keratin type I promoters, keratin type II promoters, and metallothionein promoters, as well as functional variants thereof. The cecropin proteins are well known in the art and can be derived from virtually any species, and include, for example, cecropins derived from moth (moth cecropin B) and isolated from pig (porcine cecropin P1).

The recombinant constructs of the invention are useful in driving non-tissue-specific expression of a polypeptide of interest in a fish, for example, a catfish. Where the polypeptide of interest is an anti-pathogenic polypeptide, for example, a cecropin protein or biologically active variant thereof, this constitutive expression pattern confers disease resistance throughout the entire fish. Those recombinant constructs comprising exclusively piscine promoters to drive expression of a cecropin protein or biologically active variant thereof also confer greater commercial acceptance of transgenic, disease resistant fish.

Methods for expressing a polypeptide of interest within a host cell, for example a fish cell, are also provided. The methods comprise introducing into the host cell of interest an expression cassette comprising a novel synthetic promoter sequence of the invention operably linked to a nucleotide sequence encoding the polypeptide of interest. The invention also provides a method for enhancing disease resistance in a catfish, comprising introducing into a catfish egg an expression cassette comprising a synthetic promoter of the invention or a piscine promoter operably linked to a nucleotide sequence encoding a cecropin protein or biologically active variant thereof and culturing the catfish egg under conditions suitable for maturation of the catfish egg into a catfish. In this manner, disease resistance can be conferred to different species of *Ictalurus*, including the channel catfish, the blue catfish, and the channel-blue hybrid catfish. Methods of farming transgenic catfish having enhanced disease resistance to pathogens are also disclosed.

BRIEF DESCRIPTION OF THE SEVERAL VIEWS OF THE DRAWINGS

FIG. 2 shows the relevant coding nucleotide sequences that are contained with the cecropin B-expressing vectors used in generating transgenic fish with enhanced disease resistance. The respective amino acid sequence for the encoded polypeptide is shown below each coding sequence. The single letter amino acid code is used. Slashes indicate known or predicted sites of processing of the expressed peptides. Sites of potential cleavage by leader peptidase are indicated by "\", and sites of potential cleavage by dipeptidyl peptidase are indicated by "/". The coding sequence and amino acid sequence for preprocecropin B are set forth in SEQ ID NO:12 and SEQ ID NO:11, respectively. The coding sequence and amino acid sequence for catfish Ig Vh leader/procecropin B are set forth in SEQ ID NO:21 and SEQ ID NO:22, respectively. The coding sequence and amino acid sequence for catfish Ig Vh leader/cecropin B are set forth in SEQ ID NO:23 and SEQ ID NO:24, respectively.

FIG. 3 shows the relevant coding nucleotide sequence (SEQ ID NO:27) that is contained with the cecropin P1-expressing vector used in generating transgenic fish with enhanced disease resistance. The respective amino acid sequence for the encoded polypeptide (SEQ ID NO:28) is shown below the coding sequence. The single letter amino acid code is used. The amino acid sequence shown in bold is the predicted mature sequence of the expressed peptide after processing by leader peptidase.

FIG. 4 shows the nucleotide sequence (SEQ ID NO:13) and predicted encoded amino acid sequence (SEQ ID NO:11) of a construct that encodes preprocecropin B and is driven by the synthetic promoter sequence set forth in SEQ ID NO:3.

FIG. 5 shows the nucleotide sequence (SEQ ID NO:14) and predicted encoded amino acid sequence (SEQ ID NO:11) of a construct that encodes preprocecropin B under the control of the synthetic promoter sequence set forth in SEQ ID NO:8.

FIG. 6 shows the nucleotide sequence (SEQ ID NO:35) and the encoded amino acid sequence (SEQ ID NO:11) of a construct that encodes preprocecropin B under the control of carp β-actin promoter (SEQ ID NO:29).

DETAILED DESCRIPTION OF THE INVENTION

Figure 1:
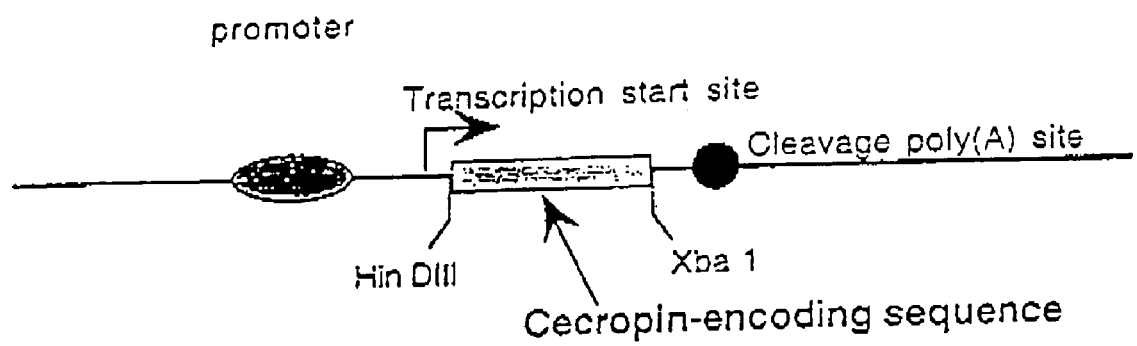
FIG. 1 shows the general scheme for the construction of vectors expressing cecropin peptides under the control of a promoter (for example, the CMV enhancer, carp β-actin promoter, or a synthetic promoter disclosed herein).

The present invention now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements.

The present invention is directed to methods and compositions that confer transgenic disease resistance to fish without using viral nucleotide sequences in the transgene. Thus, this invention confers the advantage of increasing disease resistance in fish, particularly catfish, without incurring potential consumer resistance. In this manner, the methods of the present invention utilize natural "all fish" promoters or, alternatively, "all fish" promoter elements arranged in a synthetic promoter, both of which are capable of driving expression of disease resistance genes in fish, for example, catfish. Moreover, these promoters drive constitutive, non-tissue specific expression of the transgene of interest, for example, anti-pathogenic genes, without requiring viral nucleotide sequences. These promoter attributes are useful because the fish express the anti-pathogenic protein throughout the body so pathogens cannot easily enter or replicate anywhere within the fish tissue. More advantageously, protection is conferred without the need of an inducing stimulus.

The synthetic "all fish" promoters disclosed herein confer additional advantages besides being useful to increase disease resistance in fish. When incorporated into expression cassettes, these novel synthetic promoter sequences can be used in place of naturally occurring fish promoters to drive expression of an operably linked nucleotide sequence of interest in a fish. Consequently, these novel promoters can be used to drive expression of virtually any nucleotide sequence of interest while still conferring the commercially valuable property of increased consumer acceptance to the transgenic fish. Moreover, the synthetic promoters retain the useful quality of expressing a transgene constitutively, i.e., in a non-tissue specific manner.

By "promoter" is intended a DNA sequence that directs the transcription of a gene. Usually, it is a regulatory region of DNA comprising a TATA box capable of directing RNA polymerase II to initiate RNA synthesis at the appropriate transcription initiation site for a particular coding sequence. Typically a promoter is located in the 5' region of a gene, proximal to the transcriptional start site of a coding sequence. A promoter may additionally comprise other promoter and enhancer recognition sequences generally positioned upstream or 5' to the TATA box, referred to as upstream promoter and enhancer elements, which influence the transcription initiation rate.

A synthetic promoter is an artificially created nucleotide sequence that is not produced naturally but is a man-made design, and must be introduced to an organism or to an ancestor of that organism to control expression of an operably linked nucleotide sequence. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

The synthetic promoter of the present invention comprises at least a core promoter as defined below. Additionally, the promoter may also include at least one upstream element. Such elements include upstream activation regions (UARs) and optionally, other DNA sequences that affect transcription of a structural gene, for example, synthetic upstream elements or other enhancer elements. A UAR is typically a position or orientation-dependent element that primarily directs tissue, cell-type, or regulated expression. An enhancer is a DNA regulatory element that can increase efficiency of transcription regardless of the distance or orientation of the enhancer relative to the start site of transcription.

A "core promoter" or "minimal promoter" contains the essential nucleotide sequences for expression of an operably linked coding sequence, including the TATA box and start of transcription. By this definition, a core promoter may or may not have detectable activity in the absence of specific sequences that may enhance the activity or confer tissue-specific activity. The synthetic promoter of this invention comprises as its core promoter region the goldfish minimal promoter set forth in SEQ ID NO:1 (see, for example, Wilson et al. (1991) *Mol. Immunol.* 28:449), which serves to provide promoter function. This core promoter region can be used with combinations of enhancer, upstream elements, and/or activating sequences from the 5'-flanking regions of expressible genes.

In one embodiment of this invention, the synthetic promoter comprises a goldfish minimal promoter containing a TATA box motif (SEQ ID NO:1) coupled 5' to an upstream element. The upstream element comprises at least three piscine Sp 1 binding motifs (CGGGGCGGGG; SEQ ID NO:2; see, for example, Baudler et al. (1997) *J. Biol. Chem.* 272:131–137) with novel intervening linker sequences. In one such embodiment, the synthetic promoter comprises the sequence set forth in SEQ ID NO:3. When the synthetic promoter sequence is operably linked to a nucleotide sequence of interest, for example, a coding sequence for a protein, it is capable of driving constitutive expression of the encoded product in a target host cell, for example, catfish cells. By "constitutive" is intended expression in the cells throughout a host organism, such as a fish, at most times and in most tissues. The characteristic of high non-tissue-specific expression is particularly useful when engineering a fish with enhanced disease resistance, for example, via expression of an anti-pathogenic protein, such as a cecropin polypeptide. These proteins do not harm fish during growth and development, and restrictive tissue expression may leave alternative routes of infection open to pathogens. For example, transcriptional control elements that drive expression of an anti-pathogenic protein only in the skin might not protect against bacteria entering the body via the gut or by puncture wounds.

In another embodiment, the invention provides a synthetic promoter comprising a goldfish minimal promoter containing a TATA box motif (SEQ ID NO:1) coupled to an upstream element that comprises the following elements assembled in the 5'-to-3' orientation with intervening linker sequence: at least one piscine Sp1-binding motif (CGGGGCGGGG; SEQ ID NO:2) operably linked to at least one piscine C/EBPα motif (ATAATGTTTCATCA-CACTT; SEQ ID NO:4; see, for example, Chan et al. (1997) *Eur. J. Biochem.* 247:44–51) operably linked to at least one piscine Oct motif (ATGTAAAT; SEQ ID NO:5; see, for example, Magor et al. (1997) *Immunogenetics* 46:192–198) operably linked to at least one piscine NF-κB motif (GG-GACGTCCC; SEQ ID NO:6) operably linked to at least one piscine AP-1 binding motif (ATGACTCAG; SEQ ID NO:7). In one such embodiment, the synthetic promoter comprises the sequence set forth in SEQ ID NO:8. This synthetic promoter is also useful for enhancing the transcription levels of an operably linked nucleotide sequence in the cells of a host organism, for example, in the cells of a fish.

The upstream elements described herein can be linked with the goldfish minimal promoter and/or other upstream elements, including UARs, by any conventional method that is generally known in the art as long as an operative element or promoter is constructed. The upstream elements are generally operably linked to the 5' end of the goldfish minimal promoter. In a preferred embodiment, the upstream elements are linked in close proximity to the goldfish minimal promoter. By "close proximity" is intended within from about 1 to about 50 nucleotides. However, it is recognized that more than 50 nucleotides may separate the individual upstream elements from the goldfish minimal promoter.

One or multiple copies of the upstream elements can be used with the goldfish minimal promoter. When multiple copies are utilized, they can be tandem repeats of one motif or combinations of several motifs. In this manner, the level of expression of an operably linked nucleotide sequence of interest can be controlled by the number of motifs present in the promoter construct. Thus, multiple copies of binding motifs can be used to enhance the activity of the operably linked goldfish minimal promoter.

Biologically active variants of the synthetic promoter sequences disclosed herein can also be utilized in the expression cassettes described herein. Such variant sequences will have minor variations as noted herein below that do not disrupt the promoter activity of the synthetic promoter. Preferably the variations occur outside of the region corresponding to the core goldfish minimal promoter and outside of the regions corresponding to the particular upstream elements residing in the synthetic promoters of the invention, for example, within intervening sequences that link together the core promoter and the specific upstream promoter elements (i.e., the Sp1 binding motif(s), C/EBPα motif(s), Oct motif(s), NF-κB motif(s), and AP-1 binding motif(s)). It is recognized, however, that minor modifications within the core promoter, within one or more of the upstream elements (i.e., within the Sp1 binding motif(s), C/EBPα motif(s), Oct motif(s), NF-κB motif(s), and AP-1 binding motif(s)), or within both the core promoter and one or more of the upstream elements can occur so long as the variant promoter sequence is a functional promoter.

By "functional promoter" is intended that the promoter initiates or enhances transcription. Those skilled in the art recognize that functionality of a promoter is readily determined by whether an operably linked nucleotide sequence is transcribed in the presence of the promoter. Methods of determining if transcription and translation occur are well known in the art and include measuring the mRNA production or protein production that occurs when a coding sequence for a protein of interest is placed under the control of the promoter. Necessarily, a promoter sequence incapable of inducing transcription or translation is non-functional. This invention is useful in that it describes functional synthetic promoters that are capable of initiating transcription of an operably linked coding sequence and its translation into the encoded protein. Those skilled in the art recognize that functional variants of the synthetic promoters disclosed herein are useful for expressing operably linked nucleotide sequences of interest. The term "expression" refers to biosynthesis of an encoded product. Expression involves transcription of the coding sequence into mRNA and then translation of the mRNA into one or more functional proteins or polypeptides. By "functional protein" or "functional polypeptide" is intended that the protein or polypeptide operates for its intended purpose. For example, a functional anti-pathogenic protein or anti-pathogenic polypeptide will kill or inhibit the growth of pathogens.

Promoter activity may be measured by using techniques such as Northern blot analysis, reporter activity measurements taken from transcriptional fusions, and the like. See, for example, Sambrook et al. (1989) *Molecular Cloning: A Laboratory Manual* (2d ed., Cold Spring Harbor Laboratory Press, Cold Spring Harbor, N.Y.), herein incorporated by reference. Alternatively, levels of a reporter gene such as green fluorescent protein (GFP), luciferase, beta-galactosidase (lacZ), chloramphenicol acetyl transferase (CAT), or the like produced under the control of a promoter fragment or variant promoter sequence can be measured. See, for example, Astola et al. (2003) *Gen. Comp. Endocrinol.* 134:57–61; Hwang et al. (2003) *Biochim. Biophys. Acta* 1625:11–18; Kim et al. (2000) *Gene* 252:173–181; Volckaert et al. (1994) *Mol. Mar. Biol. Biotechnol.* 3:57–69; herein incorporated by reference.

Thus biologically active variants of the disclosed synthetic promoters are also contemplated for use in the compositions and methods of the present invention. Such biologically active variants will have functional promoter activity and will have at least about 70%, generally at least about 75%, 80%, 85%, preferably at least about 90%, 91%, 92%, 93%, 94%, 95%, 96%, 97%, and more preferably at least about 98%, 99% or more sequence identity to the synthetic promoter that serves as the reference molecule, i.e., the synthetic promoter set forth in SEQ ID NO:3 or 8. It is not necessary that the variant promoter retain the same promoter activity as the reference synthetic promoter; it is sufficient that the variant promoter be functional, i.e., has the ability to drive expression of an operably linked nucleotide sequence.

Methods of alignment of sequences for comparison are well known in the art. Optimal alignment of sequences for comparison may be conducted by the algorithm of Myers and Miller (1988) *CABIOS* 4:11–17; the local homology of Smith et al. (1981) *Adv. Appl. Math.* 2:482; the homology alignment algorithm of Needleman and Wunsch (1970) *J. Mol. Biol.* 48:443–453; the search-for-similarity method of Pearson and Lipman (1988) *Proc. Natl. Acad. Sci.* 85:2444–2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. Alignment is also often performed by inspection and manual alignment.

For purposes of the present invention, percent sequence identity between any two nucleotide sequences (for example, between the synthetic promoter of SEQ ID NO:3 or SEQ ID NO:8 and a promoter sequence that is a functional variant of either of these sequences) is determined using GAP (Version 10 or later) with default parameters. GAP uses the algorithm of Needleman and Wunsch (1970) *J. Mol. Biol.* 48:443–453, to find the alignment of two complete sequences that maximizes the number of matches and minimizes the number of gaps. GAP considers all possible alignments and gap positions and creates the alignment with the largest number of matched bases and the fewest gaps. Default gap creation penalty values and gap extension penalty values in Version 10 of the Wisconsin Genetics Software Package for protein sequences are 8 and 2, respectively. For nucleotide sequences, the default gap creation penalty is 50 while the default gap extension penalty is 3.

The synthetic promoters of the invention are constructed within expression cassettes to provide for constitutive expression of an operably linked nucleotide sequence of interest. The expression cassette can be encompassed in plasmid or viral vectors for transformation of a host cell, for example fish cells. In a preferred embodiment, the synthetic promoter sequences disclosed herein are used to achieve non-tissue specific, constitutive expression of the product encoded by an operably linked nucleotide sequence of interest. In one such embodiment, the synthetic promoter set forth in SEQ ID NO:3 or SEQ ID NO:8 can be inserted into an expression cassette to obtain high levels of expression of any protein of interest.

The synthetic promoter sequences of the present invention, when assembled within a DNA construct, i.e., an expression cassette, such that the promoter is operably linked to a nucleotide sequence of interest, enable the expression of the operably linked nucleotide sequence in the cells of a fish that is stably transformed with this DNA construct. The nucleotide sequence of interest can be homologous (i.e., native) or heterologous (i.e., foreign or not naturally occurring) to the host fish that is to be transformed with such a construct.

The expression cassette will include in the 5'-to-3' direction of transcription, a synthetic promoter of the invention (for example, SEQ ID NO:3, SEQ ID NO:8, or variant thereof having promoter activity), a nucleotide sequence of interest, and a transcriptional and translational termination region (i.e., termination region) functional in fish. It is recognized that where the nucleotide sequence is a coding sequence, it is engineered within the expression cassette such that the coding sequence includes an initial start codon. Where the expression product is a fusion protein, such as a catfish immunoglobulin variable heavy chain (Ig Vh) leader/cecropin B polypeptide described herein below, the sequence encoding this fusion protein is engineered within the expression cassette to comprise a start codon placed prior to the N-terminus of the catfish Ig Vh leader-encoding sequence.

The termination region may be native to the nucleotide sequence of interest, or may be derived from another source. The expression cassette can additionally comprise a 3' enhancer(s) and/or a polyadenylation signal sequence placed downstream of the termination codon. For example, in one embodiment, the expression cassette comprises the 3' untranslated region of the bovine growth hormone placed downstream of the termination codon to increase the level of protein expression. In one such embodiment, the expression cassette comprises an operably linked 3' untranslated region of bovine growth hormone comprising the nucleotide sequence set forth in SEQ ID NO:9, which comprises a polyadenylation signal sequence comprising the AATAAA motif (nucleotides 145–150 of SEQ ID NO:9). See, for example, U.S. Pat. No. 5,122,458; Higgs et al. (1983) Nature 306:398–400); Woychik et al. (1984) Proc. Natl. Acad. Sci. USA 81:3944–3948; herein incorporated by reference.

Such an expression cassette is provided with a plurality of restriction sites for insertion of the nucleotide sequence of interest to be under the transcriptional regulation of the regulatory regions, i.e., the synthetic promoter sequences disclosed herein. The expression cassette may additionally contain selectable marker genes that facilitate selection of cells and/or organisms that have the expression cassette, preferably stably integrated within their genome.

A nucleotide sequence of interest may include any coding sequence for a protein, polypeptide, or peptide that confers a useful property to a fish cell or host fish expressing the coding sequence of interest. For purposes of the present invention, the terms "polypeptide," "peptide," and "protein" are used interchangeably to refer to a polymer of amino acid residues. The terms apply to amino acid polymers in which one or more amino acid residues is an artificial chemical analogue of a corresponding naturally occurring amino acid, as well as to naturally occurring amino acid polymers. The sequences encoding a protein of interest may be used alone or in combination with sequences encoding other proteins or agents to confer a useful property to a fish cell or host fish. Useful properties include, but are not limited to, growth enhancement, improved flavor, color and texture, cold tolerance, disease resistance, and sterility. For example, the nucleotide sequence of interest could encode a fish growth hormone, fish-growth-hormone releasing factor, the winter flounder antifreeze protein, anti-pathogenic proteins including antibodies and cecropins, or sequences that encode proteins that change the sex or ploidy of the fish.

Alternatively, the nucleotide sequence of interest that is operably linked to one of the synthetic promoters disclosed herein may be an antisense sequence for a targeted gene. By "antisense DNA nucleotide sequence" is intended a sequence that is in inverse orientation to the 5' to 3' normal orientation of that nucleotide sequence. When delivered into a fish cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired phenotypic response. Thus, the synthetic promoter sequences disclosed herein may be operably linked to antisense DNA sequences to reduce or inhibit expression of a protein in the fish such as gonadotropin releasing hormone (GnRH), myostatin and viral proteins.

In one embodiment, the expression cassette uses a synthetic promoter of the invention to drive expression of anti-pathogenic polypeptides for the purpose of conferring disease resistance to a fish. It is well known in the art that numerous anti-pathogenic polypeptides exist, including the cecropins, the magainins, the defensins, and the sarcotoxins. Because these polypeptides are amphipathic, they can disrupt the pathogen's cell membrane or wall and thus kill or inhibit the growth of the pathogen. Anti-pathogenic polypeptides can also function indirectly by disrupting the cell membrane of virally infected cells. Anti-pathogenic polypeptides as described below have little or no toxicity toward the fish cells or host fish having cells expressing the polypeptide.

Anti-pathogenic polypeptides are particularly useful for conferring disease resistance without harming or delaying the growth of transgenic fish. Those skilled in the art recognize that many classes of proteins can confer disease resistance, and the particular proteins described herein are offered by way of example, not limitation. Those skilled in the art also recognize that anti-pathogenic polypeptides may be identified using the methods to test for anti-pathogenic activity set forth below.

By "disease resistance" is intended that expression of the anti-pathogenic polypeptide avoids the disease symptoms that are the outcome of fish-pathogen interactions. That is, pathogens are prevented from causing fish diseases and the associated disease symptoms. Where the expression cassette of the invention comprises a synthetic promoter disclosed herein operably linked to a coding sequence for an anti-pathogenic polypeptide, introduction of the expression cassette into a fish can protect the resulting transgenic fish from disease, particularly those diseases that are caused by fish pathogens. By "anti-pathogenic" polypeptide is intended proteins that have anti-pathogenic activity and thus are capable of suppressing, controlling, and/or killing the invading pathogenic organism. An anti-pathogenic polypeptide will reduce the disease symptoms resulting from pathogen challenge by at least about 5% to about 50%, at least about 10% to about 60%, at least about 30% to about 70%, at least about 40% to about 80%, or at least about 50% to about 90% or greater relative to the disease symptoms that would be observed in a wild-type fish with a similar genetic component absent the ability to express a comparable level of the anti-pathogenic polypeptide. Hence, the methods of the invention can be utilized to protect fish from disease, particularly those diseases that are caused by fish pathogens.

Assays that measure anti-pathogenic activity are well known in the art, as are methods to quantitate disease resistance in fish following pathogen infection. See, for example, U.S. Pat. No. 5,998,698, herein incorporated by reference in its entirety. Such techniques include, but are not limited to, measuring the mortality rate over time for pathogen-inoculated fish, and measuring over time the inhibition of growth of pathogens in the presence of the anti-pathogenic polypeptide. For example, fish that have been genetically altered to express an anti-pathogenic polypeptide, or to express increased levels of that anti-pathogenic polypeptide, may be inoculated with a pathogen and the mortality rate plotted over time. These results can be compared to the mortality rate of controls, i.e., inoculated wild-type fish that have a similar genetic component absent the genetic alteration to express the anti-pathogenic polypeptide or to express increased levels of the anti-pathogenic polypeptide. A relative decrease in either the absolute mortality rate or average time to death versus controls demonstrates that the anti-pathogenic polypeptide conferred resistance to the pathogen. Alternatively, pathogens may be cultured in vitro in the presence of the anti-pathogenic polypeptide or cells expressing the anti-pathogenic polypeptide. A decrease in the viability of the pathogen culture compared to untreated controls demonstrates an anti-pathogenic effect of the anti-pathogenic polypeptide.

Though the following embodiments are directed to use of the synthetic promoters of the invention to drive expression of a particular class of anti-pathogenic polypeptides to achieve enhanced disease resistance in fish, it is recognized that the synthetic promoters of the invention can also be utilized to drive expression of any anti-pathogenic polypeptide of interest, including defensins, magainins, and sarcotoxins, to achieve the objective of enhanced disease resistance in fish. For a review of anti-pathogenic polypeptides, see, for example, Boman (2003) *J. Intern. Med.* 254:197–215; Zhang et al. (2000) *Vet. Res.* 31:277–296, Moore et al. (1996) *Antimicrob. Chemother.* 37:1077–1089; Merrifield et al. (1994) *Ciba Found. Symp* 186:5–20, and discussion at 20–26; U.S. Pat. No. 5,166,321; herein incorporated by reference in their entirety.

Thus, in some embodiments, the synthetic promoters of this invention are used to drive expression of a cecropin polypeptide or biologically active variant thereof as defined herein below. Cecropins are small, 30–40 residue amphipathic peptides with broad anti-pathogenic activity (see, for example, Andra et al. (2001) *Med. Microbiol. Immunol. (Berl.)* 189(3):169–173; Boman (2003) *J. Intern. Med.* 254 (3):197–215; Moore et al. (1996) *J. Antimicrob. Chemother.* 37:1077–1089). The mature cecropin polypeptide undergoes two-stage processing in the native insect cell. Cecropins are initially targeted to the endoplasmic reticulum as preprocecropins (i.e., the prepro-form of the polypeptide), and then, following cleavage of the leader peptide to generate procecropin (i.e., the pro-form of the polypeptide), four amino-terminal residues are removed by dipeptidyl peptidase to yield the mature cecropin polypeptide. A number of mature cecropins, their prepro- and pro-forms, and their respective coding sequences are known in the art, including, but not limited to, cecropin A (Qu et al. (1982) *Euro. J. Biochem.* 127:219–224; Lidholm et al. (1987) *FEBS Lett.* 226:8–12; GenBank Accession No. P01507 from *Hyalophora cecropia*, encoded by GenBank Accession No. X06672; GenBank Accession No. BAA04217 from *Bombyx mori*, encoded by GenBank Accession No. D17394) and cecropin-melittin hybrid peptides thereof (Boman et al. (1989) *FEBS Lett.* 259(1):103–106); cecropin B (Qu et al. (1982) *Eur. J. Biochem.* 127(1):219–224; van Hofsten et al. (1985) *Proc. Natl. Acad. Sci. USA* 82(8):2240–2243; Taniai et al. (1992) *Biochim. Biophys. Acta* 1132(2):203–206; Kato et al. (1993) *Insect. Biochem. Mol. Biol.* 23(2):285–290); Taniai et al. (1995) *Gene* 163(2):215–219; Yamono et al. (1994) *Biosci. Biotechnol. Biochem.* 58:1476–1478; GenBank Accession No. P01508 from *Hyalophora cecropia*, encoded by GenBank Accession No. M10309; GenBank Accession No. P04142 from *Bombyx mori*, encoded by GenBank Accession No. D11113; GenBank Accession No. P01509 from *Antheraea pernyi*) and its analogues cecropin B1 and B3 (Wang et al. (1998) *J. Biol. Chem.* 273(42):27438–27448), cecropin D (Qu et al. (1982) *Eur. J. Biochem.* 127(1):219–224; Hultmark et al. (1982) *Euro. J. Biochem.* (127:207–217; Lidholm et al. (1987) *FEBS Lett.* 226:8–12; GenBank Accession No. P01510 from *Hyalophora cecropia*, encoded by GenBank Accession No. X06673), cecropin P1 (Lee et al. (1989) *Proc. Natl. Acad. Sci. USA* 86(23):9159–9162); and cecropin polypeptides with a variety of C-terminus modifications (U.S. Pat. No. 5,166,321); the recited citations being incorporated herein by reference in their entirety.

The cecropins share a general structure of a charged N-terminal region (residues 1–21) followed by a long hydrophobic stretch (residues 22–32) that is well conserved (see, for example, U.S. Pat. No. 5,166,321). These alpha-helical molecules display their activity by permeabilizing the membranes of microbial pathogens such as bacteria (see, for example, Steiner et al. (1981) *Nature* 292:246–248; Moore et al. (1996) *J. Antimicrob. Chemother.* 37(6):1077–1089; Zhang et al. (2000) *Vet. Res.* 31(3):277–296; Chen et al. (2003) *Eur. J. Biochem.* 270(5):911–920).

In accordance with the compositions and methods of the present invention, a nucleotide sequence encoding a cecropin polypeptide of interest may be assembled into a DNA construct, i.e., an expression cassette, such that the coding sequence for the cecropin polypeptide is operably linked to a synthetic promoter of the invention, which drives expression of the cecropin coding sequence in a fish cell.

Fish having such a construct stably integrated within their genome constitutively express the cecropin polypeptide of interest, thereby enhancing their disease resistance to a number of pathogens. Such pathogens include, but are not limited to, fungi, bacteria, protozoa, and viruses. In one embodiment, catfish expressing cecropins in the manner described herein are resistant to disease after exposure to pathogens, such as *Edwardsiella ictaluri, Edwardsiella tardi, Flavobacterium columnare, Pseudomonas fluorescens, Aeromonas salmonicida, Aeromonas hydrophila,* and *Vibrio anguillarum*. However, it is well known in the art that cecropins have broad anti-pathogenic effects and can protect against other diseases as well, such as Saprolegnia fungus, and channel catfish viral disease.

Any functional cecropin polypeptide or biologically active variant thereof can be utilized in the present invention. Thus, functional cecropin polypeptides may have the form of the fully mature cecropin polypeptide (i.e., with the signal and leader sequence removed), a pre-form of the cecropin polypeptide (i.e., signal plus mature cecropin polypeptide sequence), a pro-form of the cecropin polypeptide (i.e., leader plus mature cecropin polypeptide sequence), or a prepro-form of the polypeptide (i.e., signal plus leader plus mature cecropin polypeptide sequence). Intracellular processing can remove some or all of the pre- and pro-amino acid sequences to form a mature cecropin polypeptide without adversely affecting the function of the polypeptide. The cecropin polypeptide can be a naturally occurring cecropin from any species, including cecropin isolated from pig, moths, and fish. Moreover, it is specifically contemplated that biologically active variants of a naturally occurring cecropin polypeptide, as defined herein below, may be substituted in the cassette described herein, with the same result achieved, i.e., that of conferring disease resistance in a fish to a number of pathogens.

Biologically active variants of these known mature cecropin polypeptides and the pre-, prepro- and pro-forms of the cecropins, can also be utilized in the compositions and methods of the present invention. Suitable biologically active variants can be fragments, analogues, and derivatives of the native or naturally occurring cecropin polypeptides. By "fragment" is intended a polypeptide consisting of only a part of the intact cecropin polypeptide sequence. The fragment can be a C-terminal deletion or N-terminal deletion of the cecropin polypeptide. By "analogue" is intended an analogue of either the full-length polypeptide (which can be a prececropin, preprocecropin, procecropin, or mature cecropin polypeptide) having biological activity or a fragment thereof, that includes a native sequence and structure having one or more amino acid substitutions, insertions, or deletions. Peptides having one or more peptoids (peptide mimics) are also encompassed by the term analogue (see i.e., International Publication No. WO 91/04282). By "derivative" is intended any suitable modification of the native polypeptide or fragments thereof, or their respective analogues, such as glycosylation, phosphorylation, or other addition of foreign moieties, so long as the activity is retained.

Preferably, naturally or non-naturally occurring variants of a cecropin polypeptide have amino acid sequences that are at least about 70%, 75%, 80%, preferably at least about 85%, 90%, 91%, 92%, 93%, 94%, or 95% identical to the amino acid sequence of the reference cecropin polypeptide, for example, a native or naturally occurring cecropin A, cecropin B, cecropin D, or cecropin P1, or to a shorter portion of the reference cecropin polypeptide. More preferably, the variant polypeptides are at least 96%, 97%, 98%, or at least 99% identical to the reference cecropin polypeptide.

For purposes of the present invention, percent sequence identity between any two polypeptides (for example, between the native or naturally occurring preprocecropin B of SEQ ID NO:11 and a variant of this polypeptide) is determined using GAP (Version 10 or later) with default parameters. As noted above, GAP uses the algorithm of Needleman and Wunsch (1970) *J. Mol. Biol.* 48:443–453 to find the alignment of two complete sequences that maximizes the number of matches and minimizes the number of gaps. Default gap creation penalty values and gap extension penalty values in Version 10 of the Wisconsin Genetics Software Package for protein sequences are 8 and 2, respectively. A variant polypeptide may, for example, differ from the reference cecropin polypeptide by as few as 1 to 10 amino acid residues, such as 6–10, as few as 5, as few as 4, 3, 2, or even 1 amino acid residue.

With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for sequence identity associated with conservative residue substitutions or gaps can be made (see the GAP program).

The art provides substantial guidance regarding the preparation and use of such variants, as discussed further below. A fragment of a cecropin polypeptide will generally include at least about 10 contiguous amino acid residues of the full-length cecropin polypeptide (which can be the mature cecropin sequence, or the preprocecropin, precropin, or procecropin sequence that undergoes post-translational processing to the mature cecropin polypeptide), or, preferably, about 15–25 contiguous amino acid residues of the full-length cecropin polypeptide, and most preferably about 20–30 or more contiguous amino acid residues of the full-length cecropin polypeptide.

For example, conservative amino acid substitutions may be made at one or more predicted, preferably nonessential amino acid residues. A "nonessential" amino acid residue is a residue that can be altered from the wild-type sequence of a cecropin, such as a cecropin A, B, D, or P1 polypeptide without altering its biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Such substitutions would not be made for conserved amino acid residues, or for amino acid residues residing within a conserved motif.

Alternatively, variant cecropin-encoding nucleotide sequences can be made by introducing mutations randomly along all or part of a cecropin coding sequence, such as by saturation mutagenesis, and the resultant mutants can be screened for cecropin anti-pathogenic biological activity to identify mutants that retain activity. Following mutagenesis, the encoded protein can be expressed recombinantly, and the anti-athogenic activity of the protein can be determined using standard assay techniques described herein.

When constructing the expression cassettes of the invention, the nucleotide sequence of interest can be a native coding sequence for a cecropin polypeptide of interest, or can be a variant of the native coding sequence. For example, where the cecropin polypeptide of interest is the preprocecropin B of SEQ ID NO:11, the native or naturally occurring coding sequence set forth in SEQ ID NO:10 can be utilized in the expression cassette. Alternatively, a variant of this coding sequence, such as that set forth in SEQ ID NO:12, can be utilized in the expression cassette. Variants of a nucleotide sequence of interest will have at least about 70%, 75%, 80%, preferably at least about 85%, 90%, 91%, 92%, 93%, 94%, or 95% identity to the nucleotide sequence of the reference cecropin-encoding nucleotide sequence, for example, a native or naturally occurring coding sequence for cecropin A, cecropin B, cecropin D, or cecropin P1, or to a shorter portion of the reference cecropin-encoding sequence. More preferably, the variant nucleotide sequences are at least 96%, 97%, 98%, or at least 99% identical to the reference cecropin-encoding nucleotide sequence.

For purposes of the present invention, percent sequence identity between any two nucleotide sequences of interest (for example, between the native or naturally occurring preprocecropin B coding sequence of SEQ ID NO:10 and a variant of this coding sequence) is determined using GAP (Version 10 or later) with default parameters. Default gap creation penalty values and gap extension penalty values in Version 10 of the Wisconsin Genetics Software Package for nucleotide sequences are 50 and 3, respectively.

In those instances where it is desirable to have the expressed product of the operably linked nucleotide sequence directed to a particular organelle, such as the mitochondrion, or secreted at the cell's surface or extracellularly, the expression cassette may further comprise a coding sequence for a transit peptide. In these instances, leader sequences, also known as signal peptides, from heterologous proteins may be used to create chimeras or fusions that target the cecropin polypeptide to specific cellular organelles for further processing into the mature cecropin polypeptide. In some embodiments of this invention, fusion proteins between cecropins and intracellular-targeting molecules are specifically contemplated. In this manner, an immunoglobulin variable heavy chain (Ig Vh) leader sequence from the channel catfish, or fragment of this leader sequence, is linked to the N-terminus of the cecropin polypeptide of interest. Expression of the encoded polypeptide and subsequent post-translational processing lead to production of the mature cecropin polypeptide. Leader sequences that target organelles are well known in the art. Therefore, the use of the channel catfish Ig Vh leader sequence or fragment thereof to target the endoplasmic reticulum is offered by way of example, not limitation.

In one embodiment, the expression cassette comprises a synthetic promoter of the invention (for example, SEQ ID NO:3, SEQ ID NO:8, or variant thereof having promoter activity) operably linked to a nucleotide sequence encoding preprocecropin B from *Hyalophora cecropia* (cecropia moth; GenBank Accession No. P01508; set forth in SEQ ID NO:11), for example, operably linked to the nucleotide sequence set forth as SEQ ID NO:10 (GenBank Accession No. M10309), or a variant of this coding sequence, as shown in SEQ ID NO:12. In one such embodiment, the expression cassette comprises the sequence set forth in FIG. 4 (SEQ ID NO:13). Alternatively, the expression cassette comprises the sequence set forth in FIG. 5 (SEQ ID NO:14).

In another embodiment, the expression cassette comprises a synthetic promoter of the invention (for example, SEQ ID NO:3, SEQ ID NO:8, or variant thereof having promoter activity) operably linked to a nucleotide sequence encoding procecropin B from *Hyalophora cecropia* (SEQ ID NO:16), for example, operably linked to the nucleotide sequence set forth as SEQ ID NO:15, or a variant of this coding sequence, as shown in SEQ ID NO:17. Alternatively the expression cassette comprises a synthetic promoter of the invention (for example, SEQ ID NO:3, SEQ ID NO:8, or variant thereof having promoter activity) operably linked to a nucleotide sequence encoding the mature cecropin B from *Hyalophora cecropia* (SEQ ID NO:19), for example, operably linked to the sequence set forth as SEQ ID NO:18, or a variant of this coding sequence, as shown in SEQ ID NO:20.

In alternative embodiments, the coding sequence for the preprocecropin B, procecropin B, prececropin B, or mature cecropin B can comprise alterations in the codons, such that the expression cassette encodes a biologically active variant of the prepro-, pro-, pre-, or mature cecropin B polypeptide, where the biologically active variant meets the functional and structural criteria defined above (i.e., anti-pathogenic activity and at least 70% sequence identity to the reference polypeptide).

In other embodiments, the expression cassette comprises a synthetic promoter of the invention (for example, SEQ ID NO:3, SEQ ID NO:8, or variant thereof having promoter activity) operably linked to a nucleotide sequence encoding a polypeptide that comprises the catfish immunoglobulin variable heavy chain (Ig Vh) leader linked in-frame to procecropin B or cecropin B from *Hyalophora cecropia*. In one such embodiment, the expression cassette encodes the polypeptide set forth in SEQ ID NO:22 (catfish Ig Vh leader/procecropin B), and comprises a nucleotide sequence encoding this polypeptide, for example, the nucleotide sequence set forth in SEQ ID NO:21. In an alternative embodiment, the expression cassette encodes the polypeptide set forth in SEQ ID NO:24 (catfish Ig leader/cecropin B), and comprises a nucleotide sequence encoding this polypeptide, for example, the nucleotide sequence set forth in SEQ ID NO:23. In other embodiments, the coding sequence for the catfish Ig Vh leader portion of this fusion polypeptide, and/or the coding sequence for the procecropin B or cecropin B portion of this fusion polypeptide can comprise alterations in the codons, such that the expression cassette encodes a biologically active variant of the catfish Ig leader/procecropin B or catfish Ig leader/cecropin B polypeptide, where biologically active variants meet the functional and structural criteria defined above (i.e., anti-pathogenic activity and at least 70% sequence identity to the reference polypeptide). When expressed, post-translational processing of the encoded fusion polypeptide results in production of mature cecropin B, or, where applicable, a variant of the mature cecropin B that has anti-pathogenic activity.

In other embodiments of the invention, the expression cassette comprises a synthetic promoter of the invention (for example, SEQ ID NO:3, SEQ ID NO:8, or variant thereof having promoter activity) operably linked to a nucleotide sequence encoding cecropin P1 (identified in porcine intestinal tissues; GenBank Accession No. P14661; set forth in SEQ ID NO:26), for example, operably linked to the nucleotide sequence set forth as SEQ ID NO:25. In alternative embodiments, the expression cassette comprises a synthetic promoter of the invention (for example, SEQ ID NO:3, SEQ ID NO:8, or variant thereof having promoter activity) operably linked to a nucleotide sequence encoding a polypeptide that comprises the catfish Ig Vh leader linked in-frame to cecropin P1. In one such embodiment, the expression cassette encodes the polypeptide set forth in SEQ ID NO:28 (catfish Ig Vh leader/cecropin P1), and comprises a nucleotide sequence encoding this polypeptide, for example, the nucleotide sequence set forth in SEQ ID NO:27. In other embodiments, the coding sequence for the cecropin P1, or for the catfish Ig Vh leader/cecropin P1 polypeptide, can comprise alterations in the codons, such that the expression cassette encodes a biologically active variant of the cecropin P1 polypeptide or of the catfish Ig Vh leader/cecropin P1 fusion polypeptide, where biologically active variants meet the functional and structural criteria defined above (i.e., anti-pathogenic activity and at least 70% sequence identity to the reference polypeptide). Where the construct encodes the catfish Ig Vh leader/cecropin P1 polypeptide, expression and post-translational processing result in production of mature cecropin P1, or biologically active variant thereof.

In summary, the synthetic promoters of the invention can be constructed within an expression cassette to drive expression of any operably linked nucleotide sequence of interest in a non-tissue-specific manner. The cassette may further comprise at least one additional nucleotide sequence of interest operably linked to a transcriptional and translational regulatory region, such that the additional sequence(s) is also introduced into the genome of the host organism, for example, the genome of a fish species. Other sequences of interest include, but are not limited to, selection markers that can facilitate selection of transgenic organisms. Alternatively, the additional nucleotide sequence(s) of interest and the respective regulatory region(s) can be provided on one or more additional expression cassettes.

The nucleotide sequences of interest that are to be introduced into the host organism (for example, a fish) of choice can comprise modifications that enhance expression in a particular cellular host. Such modifications include elimination of sequences encoding spurious polyadenylation signals, exon-intron splice site signals, transposon-like repeats, and other such well characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, for example, transitions and transversions, may be involved.

The synthetic promoters disclosed herein are useful for genetic engineering of fish to express any operably linked nucleotide sequence for which the encoded product confers a phenotype of interest, including a phenotype of enhanced disease resistance using the cecropin-encoding sequences described herein above. Alternatively, the same objective of creating a disease resistant fish that is acceptable to consumers can be accomplished by operably linking a naturally occurring piscine promoter sequence to a nucleotide sequence encoding the cecropin polypeptides or cecropin fusion polypeptides described above. In this manner, expression cassettes comprising cecropin-encoding sequences expressed under the control of exclusively fish promoters are useful for enhancing disease resistance in fish, for example catfish, and increasing consumer acceptance.

Thus, in alternative embodiments of this invention, naturally occurring fish promoters or biologically active variants thereof are used instead of synthetic promoters to express a cecropin polypeptide in a fish of interest. By "naturally occurring" fish promoter is intended a promoter sequence that occurs as a native regulatory sequence in fish. In these embodiments, expression cassettes are designed to comprise a naturally occurring fish promoter operably linked to a nucleotide sequence encoding a cecropin polypeptide of interest, including the cecropin polypeptides and catfish Ig leader-cecropin polypeptides described above.

Naturally occurring fish promoters of interest include, but are not limited to, a carp beta-actin promoter (for example, the promoter set forth in SEQ ID NO:29), channel catfish myostatin promoter (SEQ ID NO:30), channel catfish alpha-actin promoter (SEQ ID NO:31), channel catfish creatine kinase promoter (SEQ ID NO:32), the salmon metallothionein promoter (SEQ ID NO:33), the salmon histone H3 promoter (SEQ ID NO:34), the channel catfish keratin type I promoter, and the channel catfish keratin type II promoter.

It is recognized by those skilled in the art that having disclosed the nucleotide sequences for the naturally occurring fish promoter regions disclosed herein, it is within the state of the art to isolate and identify further regulatory elements in the 5' untranslated region upstream from the particular promoter regions identified herein. Thus, for example, where the expression cassette comprises the naturally occurring promoter regions disclosed herein, or biologically active variant thereof, it may further comprise upstream regulatory elements that confer constitutive expression of any heterologous nucleotide sequence operably linked to one of the disclosed promoter sequences. It is also recognized by those skilled in the art that regions, fragments, and entire promoters as disclosed herein may be used individually or in combination to drive expression of an operably linked cecropin-encoding sequence.

Biologically active variants of a naturally occurring fish promoter sequence can also be used in the expression cassettes of the invention to drive expression of an operably linked cecropin encoding sequence within a fish cell or whole fish. Such variants include fragments of these naturally occurring fish promoters. By "fragment" is intended a portion of the promoter nucleotide sequence. Fragments of a promoter nucleotide sequence may retain their regulatory activity. Thus, for example, less than the entire naturally occurring promoter sequences disclosed herein may be utilized to drive expression of an operably linked nucleotide sequence of interest, such as a nucleotide sequence encoding a cecropin polypeptide. It is within skill in the art to determine whether such fragments decrease expression levels or alter the nature of expression, i.e., constitutive or inducible expression.

Nucleic acid molecules that are fragments of a promoter nucleotide sequence comprise at least 15, 20, 25, 30, 35, 40, 45, 50, 75, 100, 325, 350, 375, 400, 425, 450, 500, 550, 600, 650, 700, 800 or 900 nucleotides, or up to the number of nucleotides present in the full-length promoter nucleotide sequence disclosed herein (i.e., 1571, 1586, 1208, 1799, 272, and 470 for SEQ ID NO:29, 30, 31, 32, 33, or 34, respectively). Fragments of a promoter sequence that retain their regulatory activity comprise at least 30, 35, 40 contiguous nucleotides, preferably at least 50 contiguous nucleotides, more preferably at least 75 contiguous nucleotides, still more preferably at least 100 contiguous nucleotides of the particular promoter nucleotide sequence disclosed herein. Preferred fragment lengths depend upon the objective and will also vary depending upon the particular promoter sequence.

The nucleotide sequences of such fragments will usually comprise the TATA recognition sequence of the particular promoter sequence. Such fragments may be obtained by use of restriction enzymes to cleave the naturally occurring promoter nucleotide sequence disclosed herein; by synthesizing a nucleotide sequence from the naturally occurring sequence of the promoter DNA sequence; or may be obtained through the use of PCR technology. See particularly, Mullis et al. (1987) *Methods Enzymol.* 155:335–350, and Erlich, ed. (1989) *PCR Technology* (Stockton Press, New York).

Biologically active variants of these naturally occurring fish promoters also include those that are naturally occurring variants. Naturally occurring variants of previously identified native fish promoters can be identified with the use of well-known molecular biology techniques, as, for example, with polymerase chain reaction (PCR) and hybridization techniques. Variant promoter sequences also include synthetically derived nucleotide sequences, such as those generated, for example, by using site-directed mutagenesis. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein.

Generally, variants of a naturally occurring fish promoter, such as the naturally occurring fish promoter sequence set forth in SEQ ID NO:29, 30, 31, 32, 33, 34, or 35, will have at least about 70%, generally at least 75%, 80%, 85%, preferably at least about 90%, 91%, 92%, 93%, 94%, to 95%, 96%, 97%, and more preferably at least about 98%, 99% or more sequence identity to the naturally occurring fish promoter that serves as the reference molecule. Percent identity of a nucleotide sequence is determined using GAP Version 10 (or later) with default parameters as noted above for the synthetic promoters of the invention. For nucleotide sequences, the default gap creation penalty is 50 while the default gap extension penalty is 3.

Biologically active variants include, for example, the naturally occurring fish promoter sequence having one or more nucleotide substitutions, deletions, or insertions. These variant promoter sequences will generally comprise the TATA recognition sequence of the particular naturally occurring fish promoter sequence. Promoter activity may be measured by using the techniques identified herein above with respect to the synthetic promoters of the invention, including monitoring the levels of expression of operably linked reporter genes as noted above.

In some embodiments of this invention, the expression cassette comprises a naturally occurring fish promoter (for example the promoter set forth in SEQ ID NO: 29, 30, 31, 32, 33, 34, or 35), or biologically active variant thereof, operably linked to a nucleotide sequence encoding a cecropin polypeptide selected from the group consisting of SEQ ID NO:11 (preprocecropin B), SEQ ID NO:16 (procecropin B), SEQ ID NO:19 (mature cecropin B), SEQ ID NO:22 (catfish Ig leader-procecropin B fusion polypeptide), SEQ ID NO:24 (catfish Ig leader-cecropin B fusion polypeptide), SEQ ID NO:26 (cecropin P1), and SEQ ID NO:28 (catfish Ig leader-cecropin P1 fusion polypeptide), or a biologically active variant of these cecropin polypeptides meeting the functional and structural criteria described herein above (i.e., anti-pathogenic activity and at least 70% sequence identity to the respective reference sequence). In such embodiments, the expression cassette can comprise as the operably linked cecropin-encoding sequence the sequence set forth in SEQ ID NO:10 or SEQ ID NO:12 (encoding SEQ ID NO:1), SEQ ID NO:15 or SEQ ID NO:17 (encoding SEQ ID NO:16), SEQ ID NO:18 or SEQ ID NO:20 (encoding SEQ ID NO:19), SEQ ID NO:21 (encoding SEQ ID NO:22), SEQ ID NO:23 (encoding SEQ ID NO:24), SEQ ID NO:25 (encoding SEQ ID NO:26), or the sequence set forth in SEQ ID NO:27 (encoding SEQ ID NO:28). See also the construct shown in FIG. 6 and SEQ ID NO:35.

For all of the embodiments comprising natural fish promoters disclosed above, additional promoter and enhancer elements may be included in the expression cassette to increase transcription levels of the cecropin polypeptide of interest. These elements may be synthetic or derived from fish. Such elements include, but are not limited to, the additional promoter and enhancer elements incorporated upstream of the core goldfish minimal promoter sequence of the synthetic promoters disclosed herein.

The expression cassettes described herein can be constructed within or inserted into any appropriate transformation vector for subsequent introduction into a host fish of interest. The selection of an appropriate transformation vector will depend upon the method of introducing the transformation vector into the host cell of interest. For transforming fish cells, numerous methods known in the art may be employed including transposon vectors (see, for example, U.S. Pat. No. 5,719,055; herein incorporated by reference in its entirety). In one embodiment, plasmid vectors carrying an expression cassette described herein are grown to a high copy number in bacteria. These vectors are purified, linearized, and injected into fish eggs. The eggs are allowed to mature into fry using suitable aquaculture methods, and mature fish expressing high levels of the introduced nucleotide sequence(s) of interest are bred together to stabilize the expression of these introduced sequences.

Methods for introduction of nucleotide sequences of interest and their operably linked regulatory elements in order to generate transgenic fish are well known in the art. Such methods include, but are not limited to, microinjection of linearized recombinant constructs, such as the expression cassettes described herein, into fertilized eggs, microinjection into oocytes, and electroporation. See, for example, Inoue (1992) *Mol. Mar. Biol. Biotechnol.* 1(4–5):266–270, and Dunham, R. A., et al., "Enhanced bacterial disease resistance of transgenic channel catfish, *Ictlaurus punctatus*, possessing cecropin genes," *Marine Biotechnology* 4:338–344 (2002).

The expression cassettes comprising a synthetic promoter disclosed herein operably linked to a nucleotide sequence of interest can be introduced into any fish of interest in order to achieve expression of useful proteins in the resulting transgenic fish. Where the nucleotide sequence of interest encodes an anti-pathogenic polypeptide, such as a cecropin polypeptide described herein, expression of the encoded product can be under the control of the synthetic promoters or naturally occurring fish promoters as described above. Such expression cassettes, when introduced into any fish of interest, provide the added advantage of commercial acceptability, as the regulatory elements are derived from fish.

Fish of interest include, but are not limited to carp, koi, goldfish, salmon, tilapia, and members of the catfish family, which may be of the channel, blue, or channel-blue hybrid variety. Catfish may be of the genus and species: *Ictalurus punctatus, Ictalurus furcatus, Ictalurus clarias, Ictalurus silurus, Ictalurus pangasius, Ictalurus rafinesque, Ictalurus balsanus, Ictalurus brunneus, Ictalurus catus, Ictalurus dugesi, Ictalurus lupus, Ictalurus melas, Ictalurus meridionalis, Ictalurus natalis, Ictalurus natalis erebennus, Ictalurus nebulosus, Pimelodus nebulosus, Ameiurusus nebulos, Ictalurus nebulosus catulus, Ictalurus nebulosus marmoratus, Ictalurus platycephalus, Ictalurus pricei, Ictalurus punctatu, Ameurus punctatus, Ictalurus robustus, Ictalurus simpsoni, Pimelodus argentinus, Pimelodus argystus, Pimelodus caerulescens, Pimelodus caudafurcatus, Pimelodus furcifer, Pimelodus gracilis, Pimelodus graciosuss, Pimelodus hammondi, Pimelodus houghi, Pimelodus maculates, Pimelodus megalops, Pimelodus nolatus, Pimelodus pallidus, Pimelodus vulpes, Synechoglanis beadlei punctatus, Silurus punctatus, Ictalurus serracanthus*, and hybrid crosses among these.

Production of genetically modified fish cells and whole fish expressing a gene under the control of the regulatory elements described herein combines teachings of the present disclosure with a variety of techniques and expedients known in the art. In most instances, alternate expedients exist for each stage of the overall process. The choice of expedients depends on the variables such as the plasmid vector system chosen for the cloning and introduction of the recombinant DNA molecule, the fish species to be modified, and the particular gene, promoter elements, and upstream elements used. Persons skilled in the art are able to select and use appropriate alternatives to achieve functionality. Also as known in the art, a number of fish species are transformable such that whole fish containing and expressing desired genes under regulatory control of the synthetic promoter molecules of the invention may be obtained. Truncated promoter selection and operably linked gene selection are other parameters, which may be optimized to achieve the desired expression pattern within the host fish as is known to those of skill in the art and taught herein.

It will be understood that there may be minor sequence variations within the nucleotide sequences that are incorporated into the expression cassettes described herein. Minor variations can be made without adversely affecting the function of a promoter sequence or the function of a protein encoded by an operably linked nucleotide sequence. The minor variation may occur in the promoter nucleotide sequence, in the operably linked nucleotide sequence, or within both the promoter nucleotide sequence and the operably linked nucleotide sequence. Where the operably linked nucleotide sequence is a coding sequence for a protein of interest, minor variations within the coding sequence that are due to degeneracy of the genetic code will result in expression of the same protein. Alternatively, minor variations within a coding sequence can result in expression of a protein that has substitutions, insertions, and/or deletions with respect to a reference molecule. By "minor variations" is intended that the variant sequences have at least 70%, 75%, 80%, 85%, preferably at least 90%, 91%, 92%, 93%, 94%, 95%, 96%, 97%, 98%, or even at least 99% sequence identity to a reference molecule, where sequence identity is determined as noted herein above. By "reference molecule" is intended a defined sequence used as a basis for sequence comparison. A reference sequence may be a subset or the entirety of a specified sequence; for example, a segment of a full-length synthetic or naturally occurring promoter sequence, or the full-length synthetic or naturally occurring promoter; or a segment of a full-length coding sequence, or the complete coding sequence.

Where these minor variations occur within the synthetic promoters disclosed herein, they may be determined by standard techniques that enable those of ordinary skill in the art to manipulate and bring into utility the functional units of the promoter elements necessary to direct initiation of transcription of the operably linked nucleotide sequence.

Thus, the synthetic promoter sequences or naturally occurring fish promoters utilized in the expression cassettes of the invention can include minor variations with respect to the reference molecule as long as the altered promoter sequence is capable of initiating transcription of an operably lined nucleotide sequence. Likewise, the nucleotide sequences encoding a protein of interest, for example, a cecropin polypeptide, encompass both naturally occurring coding sequences, as well as sequences that differ due to degeneration of the genetic code, which can be naturally occurring or generated via man-made intervention (for example, with site-directed mutagenesis). Furthermore, the cecropin polypeptides to be expressed using the expression cassettes disclosed herein include the mature cecropin polypeptide as well as the precercropin, procecropin, and preprocecropin forms thereof, as well as biologically active variants of these polypeptides. Such protein variants will continue to possess the desired anti-pathogenic defense protein activity. Obviously, the mutations that will be made in the DNA encoding a variant protein must not place the sequence out of reading frame and preferably will not create complementary regions that could produce secondary mRNA structure.

The following examples are offered by way of illustration and not by way of limitation.

EXPERIMENTAL

Two significant problems arise in the commercial fish market. The first problem is that disease causes hundreds of millions of dollars in damages to fish farms every year. Researchers have attempted to solve this problem by creating transgenic fish that have a commercially desirable phenotype. However, making transgenic fish creates a second problem because transgenes are routinely expressed under a viral promoter. Consumers are likely to perceive that catfish carrying viral "fragments" are unhealthy or unsafe, and thus are unlikely to buy them. Therefore, there is a need for a solution to the dilemma of creating transgenic fish that have desirable phenotypes that are also acceptable to consumers.

The present invention solves this dilemma by disclosing methods and compositions that confer the advantages of transgene expression in fish without using viral nucleotide sequences in the transgene. The transgenic system described herein thus decreases potential consumer resistance to fish bred using the compositions and methods disclosed herein. In the claimed invention two alternative methods of creating commercially acceptable fish are described. First, any valuable phenotype can be conferred to fish using the synthetic promoters described herein operably linked to a nucleotide sequence of interest in an expression cassette. These fish will be acceptable to consumers because these synthetic promoters have only fish-derived elements. Second, disease resistance in catfish can be conferred by placing naturally occurring fish promoters upstream of a nucleotide sequence encoding cecropin proteins and biologically active variants thereof. These catfish will be acceptable to consumers because the promoter (or a functional variant of the promoter) is entirely fish derived.

Peptides of mature cecropin B (SEQ ID NO:18) and mature cecropin P1 (SEQ ID NO:25) have been previously synthesized, purified by high-pressure liquid chromatography, and tested for their activity in vitro. The results of these tests demonstrate that these peptides possess the predicted bactericidal activity against *E. ictaluri* and *Aeromonas salmonicida*, which are responsible for diseases in channel catfish. See Kjull et al. (1999) *J. Fish Dis.* 22:387–394).

The toxicity of cecropin B and cecropin P1 to catfish cells was tested in vitro by titration of the peptides against the cloned catfish B lymphoblastoid cell line 1B10 (Miller et al. (1994) *J. Immunol.* 152:2180–2189). Neither of these two cecropins showed any significant toxic effect against this cell line when cultured for 5 days at cecropin concentrations ranging from 3 µg/ml up to 100 µg/ml (data not shown). The lack of toxicity of cecropins B and P1 to catfish was also confirmed by the ability to generate catfish transgenic for constructs expressing these peptides (see below).

Example 1

CMV-containing Constructs for Use in Enhancing Disease Resistance in Transgenic Catfish Transgenic catfish were constructed to demonstrate that cecropin expression confers disease resistance to catfish. Two strains of transgenic fish were bred. First, one strain of fish was engineered to express the mature cecropin B protein as set forth in SEQ ID NO:19, and a second strain of catfish was engineered to express preprocecropin B as set forth in SEQ ID NO:11.

Initially, a series of constructs were designed that would express mature cecropin B (SEQ ID NO:19), preprocecropin B (SEQ ID NO:11), or mature cecropin P1 (SEQ ID NO:26) in fish cells under regulatory control of the cytomegalovirus (CMV) enhancer. In this manner, the cytomegalovirus (CMV) enhancer was operably linked to the nucleotide sequences encoding the cecropins of interest. The CMV enhancer was chosen because it promotes strong, non-tissue specific expression of a transgene in fish cells. The constructs under the control of this enhancer express well in cultured catfish T and B cell lines (Ross et al. (1998) *J. Immunol.* 160:3874–3882). The general design scheme for these constructs and the constructs described in further examples below is shown in FIG. 1.

For cecropin B constructs, it was necessary to first target the expressed cecropin peptide to the secretory pathway, and second, induce N-terminal processing of the cecropin peptide in the endoplasmic reticulum. It is known that the cecropin peptide undergoes two-stage processing in the native insect cell. Cecropins are initially targeted to the endoplasmic reticulum as preprocecropins, and then, following cleavage of the leader peptide to generate procecropin, four amino-terminal residues are removed by dipeptidyl peptidase to yield the mature cecropin.

The first construct (CMV::preprocecropin B) was designed to express the native preprocecropin B peptide as set forth in SEQ ID NO:11 (encoded by SEQ ID NO:12). The second construct (CMV::catfish Ig Vh leader/procecropin B) was designed to express a fusion polypeptide between the catfish immunoglobulin variable heavy chain leader (Ig Vh) and procecropin B as set forth in SEQ ID NO:22 (encoded by SEQ ID NO:21). The third construct (CMV::catfish Ig Vh leader/arbitrary sequence/cecropin B) was designed to express a fusion polypeptide between the catfish Ig Vh leader and the mature cecropin B sequence as set forth in SEQ ID NO:24, with an intervening arbitrary amino acid sequence determined by the cloning strategy (encoded by SEQ ID NO:23). The fourth construct (CMV::catfish Ig Vh leader/cecropin P1) was designed to express a fusion polypeptide between the catfish Ig Vh leader and cecropin P1 as set forth in SEQ ID NO:28 (encoded by SEQ ID NO:27). Each construct was cloned between a 5' HindIII and 3' Xba1 restriction site. Details of the constructs and cecropin sequences as they appear in the constructs are shown in FIGS. 2 and 3. Expression of the cecropin products encoded by each of these constructs was under control of the CMV enhancer. Transgenic fish comprising these constructs were protected from pathogen challenges (see Example 4 below).

Example 2

Design of a Synthetic Promoter Driving Expression of a Gene Product of Interest

Although the constructs in Example 1 protected the transgenic catfish from pathogen challenges, CMV control elements are derived from a human virus and are not acceptable for agricultural use due to consumer purchasing resistance. Thus, a purely synthetic promoter was designed from fish regulatory sequences. This synthetic promoter comprised a goldfish minimal promoter containing a TATA box motif (SEQ ID NO:1; Wilson et al. (1991), *Mol. Immunol.* 28:449) coupled 5' to an upstream element. The upstream element comprised three piscine Sp1 binding motifs (CGGGGCGGGG; SEQ ID NO:2; see Baudler et al. (1997) *J. Biol. Chem.* 272:131–137) with novel intervening sequences. The minimal promoter contained the essential nucleotide sequences for expression of the operably linked coding sequence, including the TATA box and start of transcription. The synthetic promoter sequence was placed 5' of a preprocecropin B coding sequence (set forth in SEQ ID NO:12) to drive non-tissue specific, constitutive expression of this protein in fish cells. The synthetic promoter operably linked to the preprocecropin B coding sequence is shown in the sequence set forth in SEQ ID NO:13. See also FIG. 4.

The construct having this synthetic promoter operably linked to a coding sequence for preprocecropin B as described above was then cloned into a plasmid (pBS, Stratagene, 11011 N. Torrey Pines Road, La Jolla, Calif. 92037). The restriction sites flanking the polylinker site of pBS (i.e., Not 1 and Kpn 1) permitted removal of the vector sequences prior to using the coding sequences to generate transgenic fish. Thus, this cassette embodies synthetic control elements that drive gene expression at a high level and in a non-tissue specific manner. This synthetic promoter can also drive expression of any gene product of interest at high levels in a tissue non-specific manner by designing constructs that comprise the sequence for the synthetic promoter operably linked to a sequence encoding the particular gene product of interest.

Example 3

Design of an Alternative Synthetic Promoter Driving Expression of a Gene Product of Interest The sequence and structure of an alternative artificial promoter operably linked to a nucleotide sequence encoding preprocecropin B is shown in FIG. 5. The regulatory elements for designing this promoter were derived from the MT gene (Devlin et al. (1994) *Nature* 371:209–210) or the FV-1 and FV-2 actin promoters (Liu et al. (1990) *Biotechnology* S:1268–1272). FV-2 is a strong promoter while FV-1 is moderately strong (Liu et al. (1990) supra).

A series of transcription factor-binding motifs, selected for their potential to drive high-level and non-tissue specific gene expression, are placed upstream of the goldfish minimal promoter comprising a TATA box to develop an alternative artificial promoter. Specifically, the cassette encompasses a synthetic promoter comprising a goldfish minimal promoter containing a TATA box motif (SEQ ID NO:1; Wilson et al. (1991) *Mol. Immunol.* 28:449) coupled to an upstream element that contains the following elements assembled in the 5'-to-3' orientation with intervening linker sequence: a piscine Sp1-binding motif (CGGGGCGGGG; SEQ ID NO:2) operably linked to a piscine C/EBPα motif (ATAATGTTTCATCACACTT; SEQ ID NO:4; see, for example, Chan et al. (1997) *Eur. J. Biochem.* 247:44–51) operably linked to a piscine Oct motif (ATGTAAAT; SEQ ID NO:5; see, for example, Magor et al. (1997) *Immunogenetics* 46:192–198) operably linked to a piscine NF-κB motif (GGGACGTCCC; SEQ ID NO:6) operably linked to a piscine AP-1 binding motif (ATGACTCAG; SEQ ID NO:7). This promoter (set forth in SEQ ID NO:8) is operably linked 5' to a nucleotide sequence encoding preprocecropin B (for example, that shown in SEQ ID NO:12). The promoter and coding sequence are also shown in FIG. 5 (see also SEQ ID NO:14).

A construct having this alternative synthetic promoter operably linked to a coding sequence for preprocecropin (see SEQ ID NO:14) is then cloned into a plasmid (pBS, Stratagene, 11011 N. Torrey Pines Road, La Jolla, Calif. 92037) as described above. The restriction sites flanking the polylinker site of pBS (i.e., Not 1 and Kpn 1) permit removal of the vector sequences prior to using the coding sequences to generate transgenic fish. Thus, this cassette embodies synthetic control elements that drive gene expression at a high level and in a non-tissue specific manner. This synthetic promoter can also drive expression of any gene product of interest at high levels in a tissue non-specific manner by designing constructs that comprise the sequence for the synthetic promoter operably linked to a sequence encoding the particular gene product of interest.

Example 4

Catfish with Stably Incorporated Cecropin Transgenes Resist Disease Challenges

The constructs of Example 1 were introduced into fertilized catfish eggs at the one cell stage, and the resulting fry were raised and screened for the presence of the transgene.

Parental line (P1) transgenic catfish containing the CMV::preprocecropin B construct and P1 transgenic catfish containing the CMV::cecropin B constructs were spawned, and the respective transgene was transmitted to the filial ($F_1$) generation through breeding.

Specifically, channel catfish were artificially spawned in aquaria with flowing water at 26 to 27° C. by induction with carp pituitary extract (CPE). Females were injected with 2 mg/kg CPE by body weight and given a solving dose of 8 mg/kg 12 hours later to induce ovulation. Eggs were stripped from an ovulating female into a petri dish. Milt and water were added to the eggs with gentle stirring to accomplish fertilization and dispersal.

A Baekon 2000 electroporation device was used for gene transfer. Three hundred channel catfish eggs were treated at one time in 1.5 ml of buffer (TE, 0.88 mM NaCl) and 50 µg/ml of plasmid DNA containing the cecropin sequences using a 50 mm petri dish. A non-contact mode of electroporation was used with the parameters of electroporation set at 6 kV, 108 burst, 4 cycles, 27 pulses, and 160 µsec per pulse.

These P1 fish were grown in earthen ponds at the USDA-approved transgenic fish confinement facility. Individual pairs of putative transgenic fish were aquarium spawned. Individual egg masses were incubated in hatching troughs, and screened with PCR dot blot analysis (see Dunham, et al. (1992) "Transfer, expression and inheritance of salmonid growth hormone genes in channel catfish, *Ictalurus punctatus*, and effects on performance traits," *Mol. Mar. Biol. and Biotech.* 1:380–389) to ensure inheritance of the cecropin gene. Positive spawns were hatched, the fry reared in hatching troughs, and then stocked in 0.04 hectare earthen ponds in the confinement facility. Fish were fed ad libitum, harvested, and challenged at 6 months of age.

Disease Challenges

*E. ictaluri* was grown in an incubator for 24 hrs at 26° C. in BHI broth. Fish were placed communally in 500 liter aquaria for challenges. *E. ictaluri* was introduced into the tank at a concentration of $10^8$ cells/ml and the fish were immersed statically for one hour at 25° C. After that time, water (25° C.) flow was resumed. The fish were monitored for 14 days for clinical signs of *E. ictaluri* infection and mortality. Collected dead fish were necropsied to confirm cause of death and infection, and reisolation of *E. ictaluri* from these fish was attempted. Columnaris challenge occurred through a natural epizootic. A severe columnaris outbreak occurred prior to harvest in the earthen pond. Live and dead fish were collected for DNA analysis (see Dunham et al. (1992) supra) and for necropsy. Necropsy confirmed death and infection from *Flavobacterium columnare*.

In the first pathogen challenge, transgenic catfish having the CMV::cecropin B construct and non-transgenic full siblings were challenged in tanks with *Edwardsiella ictaluri*. Although both the transgenic and non-transgenic fish experienced mortality, the survival rate of the transgenic individuals was two-fold that of the controls (Table 1).

In the second pathogen challenge, transgenic catfish having the CMV::preprocecropin B construct and full, non-transgenic sibling controls were challenged with *Flavobacterium columnare*. Approximately 63% of the controls died while 0% of the transgenic fish died (Table 1). Thus, the transgene imparted complete resistance to these transgenic fish. In both experiments, no pleiotropic effects were observed for growth.

TABLE 1

Enhanced resistance to bacterial disease by transgenic channel catfish containing cecropin-encoding constructs in an epizootic and an artificial tank challenge.

| Transgene | Disease Challenge | Environment | Survival (%) Transgenic | Control |
|---|---|---|---|---|
| CMV::preprocecropin B | *F. columnare* | Pond | 100 | 27.3 |
| CMV::cecropin B | *E. ictaluri* | Tank | 40.7 | 14.8 |

These data demonstrate that catfish transgenic for cecropin constructs show enhanced resistance to both deliberate and natural challenge with pathogenic bacteria. However, transgenic fish with viral DNA sequences are not commercially acceptable so it is necessary to remove the CMV promoter and replace it with a synthetic promoter or an "all fish promoter," as described in Example 5, below.

Example 5

Catfish with Stably Incorporated Cecropin Transgenes under Control of Synthetic Promoters Resist Disease Challenges As discussed above, synthetic fish promoters operably linked to cecropin genes can be used to create transgenic catfish that are both disease resistant and commercially acceptable to consumers. To test the efficacy of the synthetic promoter of SEQ ID NO:3 and 8, these synthetic promoter sequences are operably linked 5' to a coding sequence for preprocecropin in an expression cassette as detailed in Examples 2 and 3 above. Thus, expression cassettes comprising SEQ ID NO:13 (which drives expression of preprocecropin with the synthetic promoter of SEQ ID NO:3) or SEQ ID NO:14 (which drives expression of preprocecropin with the synthetic promoter of SEQ ID NO:8) are constructed.

Using the methods described in Example 4, catfish eggs were transformed with an expression cassette comprising SEQ ID NO:13. The transgenic fry were allowed to mature under suitable conditions. The P1 line was bred creating an F1 lineage.

In a second set of experiments, catfish eggs are transformed with an expression cassette comprising SEQ ID NO:14. Transgenic fry are allowed to mature under suitable conditions. The P1 line is bred creating an F1 lineage.

Using the same methods as set forth in Example 4, F1 catfish are tested for disease resistance to pathogens of interest. Unlike the transgenic catfish in Example 4, these catfish are not transgenic for any viral DNA. Thus, these catfish are commercially acceptable, as well as being protected from disease.

Example 6

Catfish with Stably Incorporated Cecropin Transgenes under Control of Natural "All Fish Promoters" Resist Disease Challenges As discussed above, natural fish promoters operably linked to sequences encoding cecropin peptides can be also be used to create transgenic catfish that are both disease resistant and commercially acceptable to consumers. Using the methods described in Example 1, an expression cassette is constructed to comprise the fish promoter sequence of SEQ ID NO:29, 30, 31, 32, 33, 34, or 35 operably linked 5' to a cecropin-encoding nucleotide sequence, for example, the coding sequence set forth in SEQ ID NO:10 or 12 (encoding preprocecropin B of SEQ ID NO:11), the coding sequence set forth in SEQ ID NO:15 or 17 (encoding procecropin B of SEQ ID NO:16), the coding sequence set forth in SEQ ID NO:18 or 20 (encoding mature cecropin B of SEQ ID NO:19), or the coding sequence set forth in SEQ ID NO:25 (encoding mature cecropin P1 of SEQ ID NO:26). Alternatively, an expression cassette is constructed to comprise the fish promoter sequence of SEQ ID NO:29, 30, 31, 32, 33, 34, or 35 operably linked 5' to a coding sequence for a catfish Ig Vh leader-procecropin fusion, for example, the coding sequence set forth in SEQ ID NO:21 (encoding the catfish Ig Vh leader-procecropin B fusion of SEQ ID NO:22), or operably linked 5' to a coding sequence for a catfish Ig Vh leader-cecropin fusion, for example, the coding sequence set forth in SEQ ID NO:23 (encoding the catfish Ig Vh leader-cecropin B fusion of SEQ ID NO:24) or the coding sequence set forth in SEQ ID NO:27 (encoding the catfish Ig Vh leader-cecropin P1 fusion of SEQ ID NO:28). See for example, the construct shown in FIG. 6 (SEQ ID NO:35), where expression of the preprocecropin B polypeptide of SEQ ID NO:11 is controlled by the carp beta-actin promoter (SEQ ID NO:29).

Using the methods described in Example 4, catfish eggs are transfected with one of the constructs described in the present example. The transgenic fry are allowed to mature under suitable conditions. The P1 lineage is interbred creating an F1 lineage. Using the same methods as set forth in Example 4, F1 catfish are tested for disease resistance to pathogens of interest. The catfish created using these constructs are also commercially acceptable since they contain no viral DNA.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference in its entirety.

Although the foregoing invention has been described in some detail by way of illustration and example for purposes of clarity of understanding, it will be obvious that certain changes and modifications may be practiced within the scope of the invention.

That which is claimed:

1. A synthetic promoter that is functional in a fish cell, wherein said synthetic promoter comprises a nucleotide sequence selected from the group consisting of:
   a) the nucleotide sequence set forth in SEQ ID NO:3 or SEQ ID NO:8;
   b) a nucleotide sequence with at least 70% sequence identity to the nucleotide sequence set forth in SEQ ID NO:3 or SEQ ID NO:8;
   c) a nucleotide sequence with at least 80% sequence identity to the nucleotide sequence set forth in SEQ ID NO:3 or SEQ ID NO:8; and
   d) a nucleotide sequence with at least 90% sequence identity to the nucleotide sequence set forth in SEQ ID NO:3 or SEQ ID NO:8.

2. An expression cassette comprising the synthetic promoter of claim 1 operably linked in proper reading frame to a nucleotide sequence of interest.

3. A vector comprising the expression cassette of claim 2.

4. A host cell having stably incorporated in its genome the expression cassette of claim 2.

5. A method for expressing a polypeptide of interest within a host fish cell, said method comprising introducing into said host fish cell an expression cassette that comprises a functional synthetic promoter operably linked in proper reading frame to a nucleotide sequence encoding said polypeptide of interest, wherein said promoter comprises a nucleotide sequence selected from the group consisting of:
   a) the nucleotide sequence set forth in SEQ ID NO:3 or SEQ ID NO:8;
   b) a nucleotide sequence with at least 70% sequence identity to the nucleotide sequence set forth in SEQ ID NO:3 or SEQ ID NO:8;
   c) a nucleotide sequence with at least 80% sequence identity to the nucleotide sequence set forth in SEQ ID NO:3 or SEQ ID NO:8; and
   d) a nucleotide sequence with at least 90% sequence identity to the nucleotide sequence set forth in SEQ ID NO:3 or SEQ ID NO:8.

6. The method of claim 5, wherein said polypeptide of interest is an anti-pathogenic polypeptide and wherein said host fish cell is a cell of a catfish.

* * * * *